(12) United States Patent
Steliou

(10) Patent No.: US 8,741,853 B2
(45) Date of Patent: Jun. 3, 2014

(54) MITOCHONDRIA-TARGETING ANTIOXIDANT THERAPEUTICS

(76) Inventor: Kosta Steliou, Boston, MA (US)

( * ) Notice: Subject to any disclaimer, the term of this patent is extended or adjusted under 35 U.S.C. 154(b) by 273 days.

(21) Appl. No.: 12/658,575

(22) Filed: Feb. 12, 2010

(65) Prior Publication Data

US 2010/0210569 A1 Aug. 19, 2010

Related U.S. Application Data

(63) Continuation of application No. PCT/US2008/010569, filed on Sep. 10, 2008.

(60) Provisional application No. 60/994,115, filed on Sep. 17, 2007.

(51) Int. Cl.
*A01N 43/04* (2006.01)
*A61K 31/70* (2006.01)
*A01N 33/18* (2006.01)
*A01N 33/24* (2006.01)
*A61K 31/04* (2006.01)

(52) U.S. Cl.
USPC ............................................ 514/23; 514/740

(58) Field of Classification Search
None
See application file for complete search history.

(56) References Cited

U.S. PATENT DOCUMENTS 6,316,652 B1 * 11/2001 Steliou ............................ 556/42

FOREIGN PATENT DOCUMENTS

EP 0517125 A1 * 12/1992 ............. A61K 31/22

OTHER PUBLICATIONS

Hutchison et al., Bioorg. Med. Chem., 1999, 7, 1505-1511.*
Wang et al., J. Med. Chem., 1998, 41, 2207-2215.*
Poppel et al, Cancer Letters, 1997, 114, 195-202.*
Rose et al., Pharmacology & Therapeutics , 1997, 114, 195-202.*
Srinivas et al., 2007, Am J Physiol Gastrointest Liver Physiol 293: G1046-G1053.
Piermatti et al., 2008, Bioorg Med Chem 16:1444-1451.
Aich U, & Yarema KJ, 2008: In Glycoscience; Fraser-Reid B, Tatsuta K, Thiem J (eds), Springer-Verlag, Berlin, Chapter 10, p. 2133-2190.
Mertens et al., 2012, Cancer Biother Radiopharm 27:183-188.
Brown et al., 2007, Free Radical Bio Med 42:1766-1780.
Tauskela JS, 2007, IDrugs 10:399-412.

* cited by examiner

*Primary Examiner* — Layla Bland
(74) *Attorney, Agent, or Firm* — David Prashker, Esq.

(57) ABSTRACT

The instant invention constitutes an unique subject matter as a whole which has four individual aspects: (1) a class of chiral, non-racemic, synthetic carnitinoid analog carrier molecules which constitute biocompatible transport compounds not found in nature; (2) a subsequently formed, mitochondria-targeting, coupled antioxidant-carrier complex comprising an antioxidant reversibly attached to and releasable from the synthetic carrier molecule; (3) a method for introducing a biologically active antioxidant into the interior of mitochondria of a living cell for subsequent reaction with such reactive oxygen species may then be present; and (4) a system for delivering a biologically active antioxidant to the interior of mitochondria within a living cell.

16 Claims, 10 Drawing Sheets

Prior Art Fig. 1 (reproduced from Lodish et al, Molecular Cell Biology 2004, 5th edition, page 308).

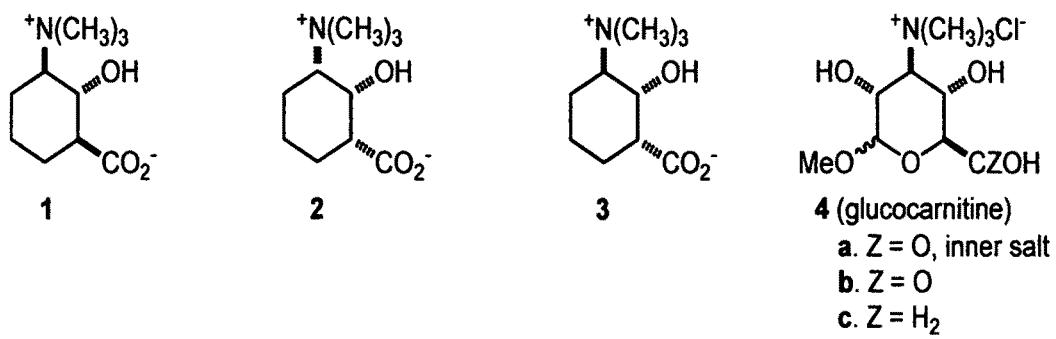
1
2
3
4 (glucocarnitine)
a. Z = O, inner salt
b. Z = O
c. Z = H₂
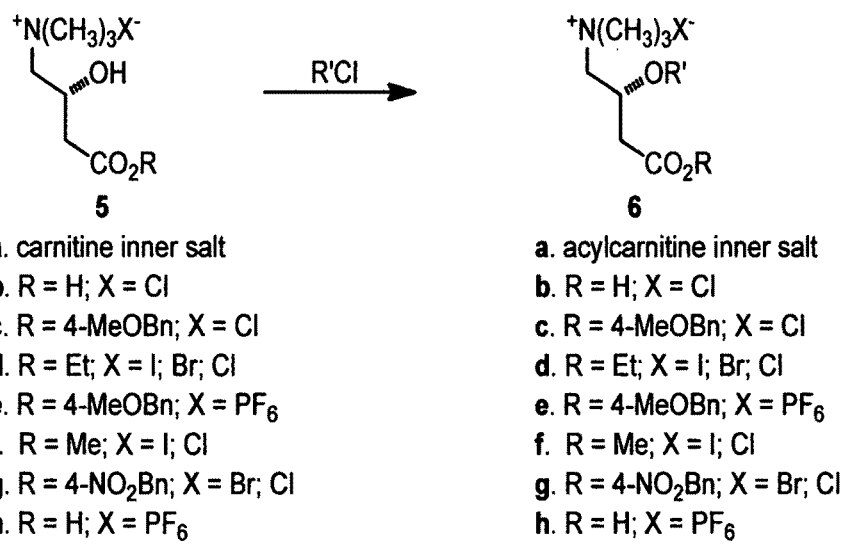
5
a. carnitine inner salt
b. R = H; X = Cl
c. R = 4-MeOBn; X = Cl
d. R = Et; X = I; Br; Cl
e. R = 4-MeOBn; X = $PF_6$
f. R = Me; X = I; Cl
g. R = 4-$NO_2$Bn; X = Br; Cl
h. R = H; X = $PF_6$
6
a. acylcarnitine inner salt
b. R = H; X = Cl
c. R = 4-MeOBn; X = Cl
d. R = Et; X = I; Br; Cl
e. R = 4-MeOBn; X = $PF_6$
f. R = Me; X = I; Cl
g. R = 4-$NO_2$Bn; X = Br; Cl
h. R = H; X = $PF_6$
Fig. 3

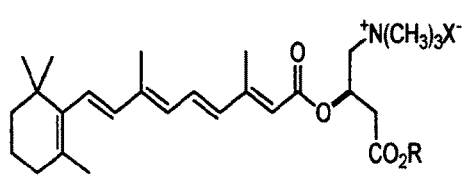
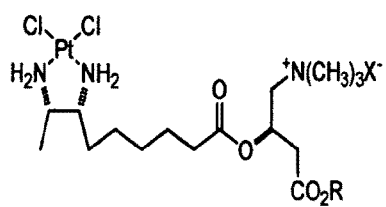
7
a. inner salt     e. R = 4-MeOBn; X = PF₆
b. R = H; X = Cl     f. R = Me; X = I; Cl
c. R = 4-MeOBn; X = Cl     g. R = 4-NO₂Bn; X = Br; Cl
d. R = Et; X = I; Br; Cl     h. R = H; X = PF₆
8
a. inner salt
b. R = H; X = Cl
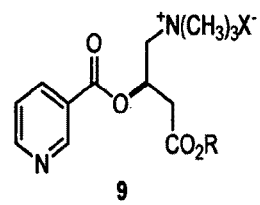
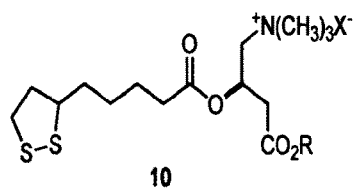
9
a. inner salt     e. R = 4-MeOBn; X = PF₆
b. R = H; X = Cl     f. R = Me; X = I; Cl
c. R = 4-MeOBn; X = Cl     g. R = 4-NO₂Bn; X = Br; Cl
d. R = Et; X = I; Br; Cl     h. R = H; X = PF₆
10
a. inner salt     e. R = 4-MeOBn; X = PF₆
b. R = H; X = Cl     f. R = Me; X = I; Cl
c. R = 4-MeOBn; X = Cl     g. R = 4-NO₂Bn; X = Br; Cl
d. R = Et; X = I; Br; Cl     h. R = H; X = PF₆
Fig. 4

Fig. 5A represents the effect of each of compounds 1-4a on $\Delta\Psi_m$.

Fig. 5B shows the dose response to $Ca^{2+}$-induced $\Delta\Psi_m$ collapse.

Fig. 6A represents the effect of each of compounds 4b, 7d, 8a, and 9c on $\Delta\Psi_m$.

Fig. 6B shows the dose response to $Ca^{2+}$-induced $\Delta\Psi_m$ collapse.

Fig. 7A shows the effect of each of compounds 9d, 10c, and 10d on $\Delta\Psi_m$.

Fig. 7B shows the dose response to $Ca^{2+}$-induced $\Delta\Psi_m$ collapse.

| Compound | 9d | 10c | 10d |
|---|---|---|---|
| $EC_{50}$ | $2.8630e^{-006}$ | $3.0630e^{-006}$ | $9.9680e^{-009}$ |

| Compound | 9d | 10c | 10d |
|---|---|---|---|
| $R^2$ | 0.1805 | 0.4171 | 0.5210 |

MITOCHONDRIA-TARGETING ANTIOXIDANT THERAPEUTICS

PRIORITY CLAIM

The present invention is a Continuation of International Patent Application PCT/US2008/010569 having an International filing date of 10 Sep. 2008; and was first filed with the U.S. Patent & Trademark Office as U.S. Provisional Patent Application Ser. No. 60/994,115 on Sep. 17, 2007. The priority and legal benefit of this first filing is expressly claimed.

FIELD OF THE INVENTION

The present invention is concerned with the abnormalities caused by mitochondrial disease in living mammals; and is directed to therapeutic methods for treating mitochondrial-based disorders and diseases using therapeutically effective mitochondria-targeted antioxidant compositions.

BACKGROUND OF THE INVENTION

A. Mitochondria

Mitochondria are organelles found in the cytoplasm of all nucleated eukaryotic cells. Each is composed of two concentric membranes, the inner membrane forming a series of folds that partially divide the interior matrix into communicating compartments. Mitochondria are generally ovoid or elongated in configuration; and uniquely contain their own genomic DNA, conventionally termed "mtDNA", which is circular in its three dimension structure and constitutes a type that is chemically separate and distinct from the chromosomal DNA in the cell's nucleus.

Mitochondrial Functions

Mitochondria undertake many roles that are central to the function and survival of the eukaryotic cell. These include at least the following:

(i) Mitochondria are the cell's principal site of energy metabolism and the main source of ATP. The primary and essential function of the mitochondria dispersed within a cell's cytoplasm is to produce adenosine triphosphate or "ATP", the chemical energy agent needed to sustain life; and typically more than 90% of a cell's requirement for ATP is supplied by its own mitochondria.

(ii) Mitochondria are also involved in heme and iron sulfur center biosynthesis, in amino acid and nitrogen metabolism, and in calcium homeostasis modulation [see for example: Stryer L, Metabolic energy and storage Part III, Chapters 17-26 pp 441-682, in *Biochemistry* 4$^{th}$ ed.; WH Freeman and Company: New York, N.Y., 1995; and Lodish et al, Cellular Energetics, Chapter 8 pp 301-350, in *Molecular Cell Biology* 5$^{th}$ ed.; WH Freeman and Company: New York, N.Y., 2004].

(iii) Mitochondria are critically involved in apoptotic cell death, being crucial in committing the cell to die by releasing pro-apoptotic factors from the intermembrane space [Nicholson D W & Thornberry N A, Life and death decisions, *Science* 229:214, 2003].

Damaged Mitochondria and Mitochondrial-Associated Diseases/Disorders

Damage to or impairment of mitochondria often causes a disruption of ATP synthesis and calcium homeostasis, which in turn will serve as a major factor leading to necrotic cell death. For these reasons, mitochondrial impairments and malfunctions act severely to disrupt the normal activities and functions of normal cells, tissues, and organs; and once impaired, malfunctioning or dysfunctional mitochondria will substantively contribute to the occurrence of a remarkably wide and varied range of clinically recognized degenerative diseases and disorders.

Mitochondria can become impaired owing to chemical changes and/or structural defects in the genes encoded by mitochondrial DNA. The vast majority of diseases of mitochondrial origin are due to defects mainly in the electron transport chain [see for example: Sarzi et al, A novel recurrent mitochondrial DNA mutation in ND3 gene is associated with isolated complex I deficiency causing Leigh syndrome and dystonia, *Am J Med Genet Part A* 143A:33-41, 2007; Martin L J, Mitochondriopathy in Parkinson disease and amyotrophic lateral sclerosis, *J Neuropathol Exp Neurol* 65:1103-1110, 2006; and DiMauro S, Mitochondrial myopathies, *Curr Opin Rheumatol* 18:636-641, 2006].

These injuries are the result of damaged or mutated proteins being incorporated into the electron transport complexes. The damaged proteins can be any one of the 13 that are encoded by the mitochondrial genome or ones being encoded by a nuclear gene since the complexes are composed of subunits of each. Also, because such damage often affects the ability of the mitochondria to make ATP, the particular diseases or disorders will generally appear and be manifested as degenerating abnormalities in those cells and tissues having a high ATP demand, such as neurons or muscle [DiMauro S & Schon E A, Mitochondrial respiratory-chain diseases, *N Engl J Med* 348:2656-2668, 2003]. In addition, with those clinical conditions having an underlying genetic causative basis which directly affect mitochondrial function, such mitochondrial damage typically contributes to the pathology of the disorders.

Merely illustrating the currently recognized range and variety of mitochondrial-associated diseases and disorders are mitochondrial dementia, Parkinson's disease, Huntington's disease, Alzheimer's disease, amyotrophic lateral sclerosis, diabetes, steatohepatitis, sepsis, retinopathies, and ischemia-reperfusion injury [see for example: Finsterer J, Cognitive decline as a manifestation of mitochondrial disorders (mitochondrial dementia), *J Neurol Sci* 272:20-33, 2008; Keating D J, Mitochondrial dysfunction, oxidative stress, regulation of exocytosis and their relevance to neurodegenerative diseases, *J Neurochem* 104:298-305, 2008; Peterson et al, Impaired mitochondrial activity in the insulin-resistant offspring of patients with type-2 diabetes, *N Engl J Med* 350:664-671, 2004; Caldwell et al, Mitochondrial abnormalities in non-alcoholic steatohepatitis, *J Hepatol* 31:430-434, 1999; Leonard J V & Schapira A H V, Mitochondrial respiratory chain disorders I: mitochondrial DNA defects, *Lancet* 355:389-394, 2000, Schaefer A M, Prevalence of mitochondrial DNA disease in adults, *Ann Neurol* 63:35-39, 2008; and Wallace D C, Mitochondrial disease in man and mouse, *Science* 283:1482-1488, 1999].

The Overlooked Relationships Existing Between Mitochondrial-Associated Diseases/Disorders and Mitochondrial-Impaired Clinical Cancers When the living cells in a tissue collectively experience sustained mitochondrial impairment, severe deleterious consequences usually result. Energy demanding tissues, such as the brain and the musculature, typically bear the brunt of the injury; and symptoms of such degenerative disorders are among the first to become manifest and clinically evident

[DiMauro et al, Approaches to the treatment of mitochondrial diseases, *Muscle Nerve* 34:265-283, 2006; and Kidd P M, Neurodegeneration from mitochondrial insufficiency: Nutrients, stem cells, growth factors, and prospects for brain rebuilding using integrative management, *Alt Med Rev* 10:268-293, 2005].

Moreover, another life-sustaining function which normal mitochondria are able to perform is "apoptosis" [Orrenius et al, Mitochondrial oxidative stress: Implications for cell death, *Annu Rev Pharmacol Toxicol* 47:143-183, 2007]. Apoptosis is conventionally defined as an intrinsic programmed sequence of specific chemical events leading to the self-destruction of a damaged cell or cells that are no longer needed for the proper maintenance of the tissue or organ.

Cancer cells, however, do not appear to have any preprogrammed death sequence or apoptosis functionality. It is no accident, therefore, that cancerous tissues are replete with abnormal cells which have malfunctioning or dysfunctional mitochondria; and it is now believed that these damaged mitochondria play a causative role in the disease initiating process, particularly in the metastasis of tumor cells [Verma M & Kumar D, Application of mitochondrial genome information in cancer epidemiology, *Clinica Chimica Acta* 383: 41-50, 2007; Czarnecka et al, Cancer as a mitochondriopathy, *J Cancer Molecules* 3:71-79, 2007; Bucay A H, The biological significance of cancer: Mitochondria as a cause of cancer and the inhibition of glycolysis with citrate as a cancer treatment, *Medical Hypothesis* 69:826-828, 2007; Barry I, Trading in mitochondria, *Nat Rev Cancer* 8:409, 2008].

It is now also recognized that cancers and mitochondrial-associated diseases/disorders, albeit disparate afflictions, nevertheless share a primary and dominant feature in common: A failure of normal aerobic cellular respiratory activity within the affected cells and tissues.

However, there is a more subtle and distinctive difference as well. In mitochondrial-associated diseases and disorders, the impaired mitochondria and the altered respiration are typically the result of changes to or abnormalities in their mtDNA; whereas in cancerous cells, the impaired mitochondria in and the altered respiration of the abnormal cells is driven and controlled by the Warburg effect.

The Warburg Effect

The Warburg effect identifies a marked change in the manner by which ATP is produced by a cell; and indicates a chemical shift away from the higher oxidative-phosphorylation aerobic process inside the mitochondria to a much smaller ATP production by anaerobic glycolysis in the cell's cytoplasm, even when the existing oxygen supply to the cell is sufficient for aerobic respiration to occur. Cytoplasmic glycolysis, by definition, is the anaerobic respiration process of enzymatically converting each molecule of glucose into two molecules of pyruvate with only a modest production and release of energy (i.e., 2 ATP molecules). In comparison, the aerobic respiration production of ATP by mitochondria in a normal cell yields 15 times more ATP per molecule of glucose. Thus, the Warburg effect—constituting a chemical shift to the anaerobic energy metabolism process with a concomitant major reduction of ATP quantity production—is highly associated with and has become markedly indicative of tumor cells [see for example: Kroemer G & Pouyssegur J, Tumor cell metabolism: Cancer's Achilles' heel, *Cancer Cell* 13:472-482, 2008; Kritikou E, Warburg effect revisited, *Nat Rev Mol Cell Biol* 8:247, 2008; Godinot et al, Actuality of Warburg's views in our understanding of renal cancer metabolism, *J Bioenerg Biomembr* 39:235-241, 2007; Wu et al, Multiparameter metabolic analysis reveals a close link between attenuated mitochondrial bioenergetic function and enhanced glycolysis dependency in human tumor cells, *Am J Physiol Cell Physiol* 292:C125-C136, 2007; Lane N, Power games, *Nature* 443:901-903, 2006; Warburg O, On the origin of cancer cells, *Science* 123:309-314, 1956; Warburg et al, Über den stoffwechsel der tumoren, *Biochem Z* 152:319-344, 1924].

As illustrated and summarized by Prior Art FIG. 1, the Warburg effect stands in direct contrast to normal aerobic oxidation processes. Under normal cellular metabolic conditions, the pyruvate molecules produced by glycolysis are actively transported from the cytosolic space into the inner matrix of the cell's mitochondria. Once within the mitochondrial inner matrix, each pyruvate molecule is reacted through a series of enzymatic transformations involving alpha-lipoic acid to yield acetyl CoA, which feeds the citric acid (Krebs) cycle. When an excess of acetyl CoA builds up inside the mitochondrion, the acetyl CoA is shuttled out to the cytosolic side through the intermediacy of a carnitine ester.

In the cytosol, Fatty Acid Synthase uses up the acetyl CoA to make fatty acyl CoA—thereby providing a pathway for excess glucose (not needed for glycogen storage in the liver) to be converted into energy storing fatty acids. Again, through the intermediacy of a carnitine ester, the accumulated fatty acyl CoA is moved into the inner matrix of the mitochondria where it is consumed in the electron transport chain [see Prior Art FIG. 1] to produce a net of 106 ATP per 16-carbon (palmitic) fatty acid length.

Via this mechanism, the normal cell produces more than 3.5 times the amount of energy obtained per molecule of completely oxidized glucose in the mitochondrion and 53 times the amount of energy obtained by glycolysis in the cytoplasm.

A Secondary Consequence

In addition, there is a secondary effect and feature which is often overlooked or ignored. In tumor cells, when the complete aerobic oxidation of glucose is inhibited and energy production instead relies on cytoplasmic glycolysis (the Warburg effect), the activity of the cell's mitochondria effectively becomes suppressed. This suppression of the tumor cell's mitochondria in turn causes a secondary outcome and consequence: the induction of a state of apoptosis resistance. The tumor cell is thus able to avoid the prearranged sequence of events leading to its self-destruction that is part of every normal cell, owing to the tumor cell's reliance and use of cytoplasmic glycolysis (the Warburg effect) for energy production.

The nature of apoptosis resistance in a tumor cell is illustrated and evidenced by the following: Alpha-Lipoic acid stimulates the natural uptake of pyruvate from the cytosol into the mitochondrial matrix and is part of the pyruvate dehydrogenase complex that drives the citric acid cycle. It is an essential cofactor in metabolism; and neither this cofactor nor its principal metabolic end-product [(R)-4,6-bis(methylthio) hexanoic acid] is toxic to normal cells, even when substantial amounts (up to 600 mg/day) of alpha-lipoic acid supplements are added to the diet. On the other hand, in human tumor cell lines FaDu and Jurkat, as well as with a Ki-v-Ras-transformed Balb/c-3T3 murine mesenchymal cell line, the published studies show that the introduction of alpha-lipoic acid induces apoptosis [Van de Mark et al, α-Lipoic acid induces $p27^{Kip}$-dependent cell cycle arrest in non-transformed cell lines and apoptosis in tumor cell lines, *J Cell Physiol* 194: 325-340, 2003].

Stem Cell Differentiation

Stem cells are fundamental components in body development and growth. The enduring presence of this cell type in the body is necessary for wound-healing, and in the normal maintenance and regeneration of bone, blood and tissues throughout one's lifespan.

Tumor cells and stem cells have in common an ability to self-reproduce indefinitely. They both also have in common a suppressed mitochondrial metabolism that shifts production of ATP to cytoplasmic glycolysis. Proliferating tumor cells adapt to aerobic glycolysis (the Warburg effect), whereas stem cells suppress their metabolism as a means for maintaining their "sternness". Furthermore, while normalizing mitochondrial metabolic activity in tumor cells reestablishes their apoptotic susceptibility, in embryonic stem cells, mitochondrial metabolism modulates the cell's capacity to differentiate [see for example: Schieke et al, Mitochondrial metabolism modulates differentiation and teratoma formation capacity in mouse embryonic stem cells, *J Biol Chem* 10.1074/jbc.M802763200 (Aug. 18, 2008); Vermeulen et al, Cancer stem cells—old concepts new insights, *Cell Death Differ* 15:947-958, 2008; Scadden D T, The stem-cell niche as an entity of action, *Nature* 441:1075-1079, 2006; Van de Mark et al, α-Lipoic acid induces p27$^{Kip}$-dependent cell cycle arrest in non-transformed cell lines and apoptosis in tumor cell lines, *J Cell Physiol* 194:325-340, 2003].

Thus, mitochondria-targeting agents that modulate mitochondrial activity in-vivo may also target cancer stem cells. Additionally, controlling ex-vivo differentiation by modulating mitochondrial activity in embryonic stem cells, as well as stem cells not yet fully differentiated, will greatly expand their clinical utility [Kidd P M, Neurodegeneration from mitochondrial insufficiency: Nutrients, stem cells, growth factors, and prospects for brain rebuilding using integrative management, *Alt Med Rev* 10:268-293, 2005].

Reactive Oxygen Species ("ROS")

In nearly all cases where mitochondrial malfunction or dysfunction contributes to the disease or disorder, a major cause of damage is the increased presence of reactive oxygen species or "ROS", which are created by the mitochondria themselves, either directly as a consequence of the impairment or damage, or as a secondary result of other malfunctions [Raha S & Robinson B H, Mitochondria, oxygen free radicals, disease and ageing, *Trends Biochem Sci* 25:502-508, 2000; Finkel T, Radical medicine: treating ageing to cure disease, *Nat Rev Mol Cell Biol* 6:971-976, 2005; Balaban et al, Mitochondria, oxidants, and aging, *Cell* 120:483-495, 2005].

A principal type of "ROS" is the superoxide—conventionally defined as an anion formed by the reduction of a molecule of oxygen by one electron. Often, the superoxide entity is a byproduct of the respiratory chain, although other superoxide sources within mitochondria typically include: α-glycerophosphate dehydrogenase; the electron transfer flavoprotein/electron transfer flavoprotein-ubiquinone oxidoreductase system in β-oxidation; α-ketoglutarate dehydrogenase; and dihydroorotate dehydrogenase. The intermembrane space protein p66Shc and monoamine oxidase on the mitochondrial outer membrane can also produce hydrogen peroxide [Miwa et al, Superoxide and hydrogen peroxide production by *Drosophila* mitochondria, *Free Radic Biol Med* 35:938-948, 2003; St-Pierre et al, Topology of superoxide production from different sites in the mitochondrial electron transport chain, *J Biol Chem* 277:44784-44790, 2002; Starkov et al, Mitochondrial alpha-ketoglutarate dehydrogenase complex generates reactive oxygen species, *J Neurosci* 24:7779-7788, 2004; Forman H J & Kennedy J, Dihydroorotate-dependent superoxide production in rat brain and liver. A function of the primary dehydrogenase, *Arch Biochem Biophys* 173:219-224, 1976; Giorgio et al, Electron transfer between cytochrome c and p66shc generates reactive oxygen species that trigger mitochondrial apoptosis, *Cell* 122:221-233, 2005; Sandri et al, Hydrogen peroxide production by monoamine oxidase in isolated rat-brain mitochondria: its effects on glutathione levels and $Ca^{2+}$ efflux, *Biochim Biophys Acta* 1035:300-305, 1990].

It will be noted that superoxide itself is deemed to be not particularly reactive—although superoxides can react with aconitase to release ferrous iron; and can also react with nitric oxide to form the reactive and highly damaging oxidant, peroxynitrite. Superoxides usually revert into hydrogen peroxide, a compound which itself can react with ferrous iron to yield the very reactive hydroxyl (.OH) radical [see for example: Sawyer D T & Valentine J S, How super is superoxide?, *Acc Chem Res* 14:393-400, 1981; Vasquez-Vivar et al, Mitochondrial aconitase is a source of hydroxyl radical. An electron spin resonance investigation, *J Biol Chem* 275: 14064-14069, 2000; Beckman et al, Apparent hydroxyl radical production by peroxynitrite: implications for endothelial injury from nitric oxide and superoxide, *Proc Natl Acad Sci USA* 87:1620-1624, 1990].

Mitochondrial generated reactive oxygen species or "ROS" will cause severe damage to mitochondrial proteins, lipids, and DNA—thereby disrupting mitochondrial function and also causing the ROS to flow into the cytosol of the cell. There appears to be a series of intrinsic mitochondrial antioxidant defenses able to intercept ROS and to minimize oxidative damage; but excessive production of ROS or a disruption of the antioxidant defenses typically leads to extensive oxidative damage to the mitochondria [Fridovich I, Superoxide anion radical ($O_2^-$.), superoxide dismutases, and related matters, *J Biol Chem* 272:18515-18517, 1997; Murphy M P & Smith R A J, Drug delivery to mitochondria: the key to mitochondrial medicine, *Adv Drug Deliv Rev* 41:235-250, 2000; Finkel T, Radical medicine: treating ageing to cure disease, *Nat Rev Mol Cell Biol* 6:971-976, 2005].

Mitochondrial Targeting Systems

During the past few years, the patent literature and a number of outstanding scientific review articles have been published that discuss various ways to bring drugs or chemicals into mitochondria. Among these published reviews are the following, the texts of which are individually expressly incorporated by reference herein: U.S. Patent Publication No. 2007/0203332; Hoye et al, Targeting mitochondria, *Acc Chem Res* 41:87-97, 2008; Tauskela J S, Drug evaluation: MitoQ—a mitochondrial-targeted antioxidant, *IDrugs* 10:399-412, 2007; Fink et al, Hemigramicidine-TEMPO conjugates: Novel mitochondria-targeted anti-oxidants, *Biochem Pharmacol* 74:801-809, 2007; Neuzil et al, Vitamin E analogs as a novel group of mitocans: Anti-cancer agents that act by targeting mitochondria, *Mol Aspects Med* 28:607-645, 2007; Murphy M P & Smith R A, Targeting antioxidants to mitochondria by conjugation to lipophilic cations, *Annu Rev Pharmacol Toxicol* 47:629-656, 2007; Yamada et al, Mitochondrial drug delivery and mitochondrial disease therapy—an approach to liposome-based delivery targeted to mitochondria, *Mitochondrion* 7:63-71, 2007; Mukhopadhyay A & Weiner H, Delivery of drugs and macromolecules to mitochondria, *Adv Drug Deliv Rev* 59:729-738, 2007; Weissig et al, Liposomes and liposome-like vesicles for drug and DNA delivery to mitochondria, *J Liposome Res* 16:249-264, 2006; Torchilin V P, Recent approaches to intracellular delivery of drugs and DNA and organelle targeting, *Annu Rev Biomed*

Eng 8:343-375, 2006; Gray et al, Mitochondria of protists, *Annu Rev Genet.* 38:477-524, 2004; and Murphy M P & Smith R A, Drug delivery to mitochondria: the key to mitochondrial medicine, *Adv Drug Deliv Rev* 41:235-250, 2000.

In addition, many research investigations have been conducted which seek therapies for treating specific disorders and disease states. Exemplifying and illustrating such publications are the following: Rapoport et al, TAT-mediated delivery of LAD restores pyruvate dehydrogense complex activity in the mitochondria of patients with LAD deficiency, *Mol Ther* 16:691-697, 2008; Kyriakouli et al, Progress and prospects: gene therapy for mitochondrial DNA disease, *Gene Ther* 15:1017-1023, 2008; Michelakis E D, Mitochondrial medicine: A new era in medicine opens new windows and brings new challenges, *Circulation* 117:2431-2434, 2008; Shen et al, R-α-Lipoic acid and acetyl-L-carnitine complimentary promote mitochondrial biogenesis in murine 3T3-L1 adipocytes, *Diabetologia* 51:165-174, 2008; Vergani et al, Cultured muscle cells display defects of mitochondrial myopathy ameliorated by anti-oxidants, *Brain* 130:2715-2724, 2007; Westphal et al, A therapeutic role for sirtuins in diseases of aging?, *Trends Biochem Sci* 32:555-560, 2007; DiMauro et al, Approaches to the treatment of Mitochondrial Diseases, *Muscle Nerve* 34:265-283, 2006; and Kidd P M, Neurodegeneration from mitochondrial insufficiency: Nutrients, stem cells, growth factors, and prospects for brain rebuilding using integrative management, *Alt Med Rev* 10:268-293, 2005.

Carnitine

Chemically, carnitine is L-(3R)-3-hydroxy-4-(trimethylammonio)butanoate or (2R)-3-carboxy-2-hydroxy-N,N,N-trimethyl-1-propanaminium inner salt. This compound occurs naturally in the body and serves in-vivo as an acyl carrier compound, transporting acyl groups across the inner mitochondrial membrane and equilibrating acyl CoA on both sides of the membrane Naturally Occurring Carnitine Carnitine is an essential nutrient of metabolic oxidation because it mediates the transport of medium-chain and long-chain fatty acids across mitochondrial membranes; facilitates the oxidation of these transported fatty acids; and then carries intermediate toxic products out of the mitochondria, thereby preventing their accumulation.

Carnitine is also considered to be a "conditionally" essential nutrient, because under certain in-vivo conditions its demand may exceed the living host's capacity to produce it. However, carnitine is typically found concentrated in tissues that utilize fatty acids as their primary dietary fuel, such as within skeletal and cardiac muscle; and, in general, healthy adults do not require a dietary intake of carnitine (from meat and dairy sources) because carnitine is endogenously produced in functionally adequate amounts by the liver and kidneys of the living body.

As a chemical composition, carnitine may exist in both L- and D-enantiomeric forms. However, only the L-enantiomer is the natural and biologically active form distributed in nature. Research investigations conducted over the last three decades have provided a better understanding of the biochemical roles for carnitine [see for example: Sewell A C & Böhles H J, Acylcarnitines in intermediary metabolism, *Eur J Pediatr* 154:871-877, 1995; and Hutchison et al, Stereoselective synthesis of a conformationally defined cyclohexyl carnitine analogue that binds CPT-1 with high affinity, *Bioorg Med Chem* 7:1505-1511, 1999].

Presently these roles include: mitochondrial long-chain fatty acid oxidation, buffering the mitochondrial acyl CoA/CoA couple, a scavenger system for acyl groups, and branched-chain amino acid metabolism [Rebouche C J, Carnitine function and requirements during the life cycle, *FASEB J* 6:3379-3386, 1992].

Acylcarnitine

Acylcarnitine is the naturally occurring, combined form of the inner carnitine salt joined to an organic fatty acid residue "RCO", wherein R may be an aliphatic, alicyclic, or aromatic moiety. As it exists in nature, acylcarnitine is a high-energy moiety, fatty acid O-ester of carnitine that mediates the transfer of fatty acyl groups from the cytoplasm to the mitochondrial matrix for oxidation purposes. It is recognized that fatty acids that enter a cell must be activated before they are metabolized. This activation process constitutes a fatty acid reacting with coenzyme A ("CoASH") to form acyl coenzyme A thioester ("fatty acyl CoA").

However, the mitochondrial membranes themselves are impermeable to such acyl CoA thioesters. Nevertheless, transportation of such fatty acyl groups can be accomplished by carnitine, which functions as a shuttle across the mitochondrial membranes. Accordingly, naturally existing carnitine accepts a fatty acyl group at the cytoplasmic side to form acylcarnitine; and then (after passing through the mitochondrial membrane) gives up the fatty acyl group at the matrix side to CoASH, thereby yielding fatty acyl CoA and carnitine [Stryer L, Fatty Acid Metabolism, Chapter 24 pp 603-628, in *Biochemistry* $4^{th}$ ed.; WH Freeman and Company: New York, N.Y., 1995].

In a similar fashion, carnitine is also used in the transport of acetyl groups from the mitochondrial matrix to the cytoplasm, where the two carbon fragments can be used for either new fatty acid formation or cholesterol synthesis [Bieber L L, Carnitine, *Ann Rev Biochem* 57:261-283, 1988; Bremer J, Carnitine-metabolism and functions, *Physiol Rev* 63:1420-1480, 1983; Bieber et al, Possible functions of short-chain and medium-chain carnitine acyltransferases, *Fed Proc* 41:2858-2862, 1982].

Carnitine and its Direct Derivatives

Carnitine and its direct derivatives have been investigated as metabolites for animals and for human diet and therapy. Merely representing such research efforts are the following publications: A nutritional composition for enhancing skeletal muscle adapted to exercise training [U.S. Pat. No. 4,687,782]; A pharmaceutical acylcarnitine composition for treating peripheral vascular diseases [U.S. Pat. No. 4,343,816]; A nutritional and dietary composition [U.S. Pat. No. 5,560,928]; An enteral nutritional composition having a balanced amino acid profile [U.S. Pat. No. 5,504,072]; Compositions for increasing intracellular ATP levels, increasing physical performance levels, and increasing the rate of wound repair [U.S. Pat. No. 5,391,550]; and methods for treating insulin-like growth factor and bone loss associated with aging [U.S. Pat. No. 5,240,961].

In addition, other carnitine-derivative compounds have been prepared and evaluated for their functional properties and characteristics. Many of these are the result of investigations which have employed both carnitine and some carnitine-like derivatives in order (a) to understand better what is the precise mechanism of action for the naturally occurring carrier compound; and/or (b) to identify the role it plays in fatty acid oxidation and energy production; and/or (c) to evaluate what are the limits of functional activity for the naturally occurring carnitine molecule.

Among the better known examples of such published studies and developments are the following: A carnitine transport carrier isolated from the human testis [Enomoto et al, Molecular identification of a novel carnitine transporter specific to human testis. Insights into the mechanism of carnitine recognition, *J Biol Chem* 277:36262-36271, 2002]; and a carnitinoid structure embedded in anthopleurine, the natural alarm pheromone isolated from *Anthopleura elegantissima* [Musich J A & Rapoport H, Synthesis of anthopleurine, the alarm pheromone from *Anthopleura elegantissima, J Am Chem Soc* 100:4865-4872, 1978].

Carnitine and its immediate derivatives have also been occasionally investigated for their potential use as pharmacologically active compositions. Merely exemplifying such instances are: Acylcarnitines having a marked antitumor activity [U.S. Pat. No. 6,673,839]; Carnitine-like agents carrying cisplatin derivatives which are used as antitumor agents [U.S. Pat. No. 6,316,652]; A cleavable compound comprising carnitine bound via a hydrolysable linker to a lipoic acid derivative or to dihydrolipoic acid [PCT International Publication No. WO 2007/095760]; Esters of L-carnitine and alkanoyl L-carnitines used as cationic lipids for the delivery of pharmacologically active compounds [PCT International Publication No. WO 2000/61543]; Cyclohexyl homologues of carnitine [Hutchison et al, Stereoselective synthesis of a conformationally defined cyclohexyl carnitine analogue that binds CPT-1 with high affinity, *Bioorg Med Chem* 7:1505-1511, 1999; Brouillette et al, Synthesis and enzymatic evaluation of conformationally defined carnitine analogs, *J Org Chem* 59:4297-4302, 1994]; and a carnitine-fatty acid ester derivative obtained by alkaline reduction of a fermented admixture of fish, soybeans and yeast, which is useful for neutral fat reduction and as an antiobesity agent [Japanese Patent Publication No. 2007-204447].

Enhancements of Carnitine Mediated Metabolism

Today, there is also a number of differently prepared formulary and dietary compositions for enhancing carnitine mediated metabolism within mitochondria; and some of these employ other specified antioxidants or vitamins in combination with naturally occurring carnitine. Among these are the following representative examples: A chemical composition combining L-carnitine and alpha-lipoic acid together as an active ingredient for either the prevention or the therapeutic treatment of pathological states induced by free radicals is alluded to in [U.S. Pat. No. 6,365,622]; A dietary composition using a combination of a carnitine and a mitochondrially active antioxidant which physiologically comprises a metabolically reactive thiol group for enhancing metabolism and alleviating oxidative stress [U.S. Pat. No. 5,916,912]; Esters of L-carnitine or alkanoyl L-carnitines useful as cationic lipids for the intracellular delivery of various pharmacologically active compounds [PCT International Patent Publication No. WO 00/6153]; Synthesis and characterization of long-chain alkyl acyl carnitine esters as potentially biodegradable cationic lipids for use in gene delivery [Wang et al, Synthesis and characterization of long chain alkyl acyl carnitine esters. Potentially biodegradable cationic lipids for use in gene delivery, *J Med Chem* 41:2207-2215, 1998]; and Synthesis and characterization of carnitine-nitro derivatives [Piermatti et al, Synthesis and characterization of carnitine-nitro derivatives, *Bioorg Med Chem* 16:1444-1451, 2008].

Antioxidant Compositions

Mitochondrial oxidative damage contributes to a broad range of degenerative diseases and disorders. Consequently, the inhibition of mitochondrial oxidative damage using an antioxidant agent has been put forward as a possible therapeutic strategy; and a number of surprisingly different antioxidant compositions for avoiding or diminishing mitochondrial oxidative damage have been suggested, as reported by the published medical articles, printed scientific papers, and issued patents to date.

Traits and Attributes

By common definition, an antioxidant is a chemical composition that retards or inhibits the oxidation of another substance to which it is added.

However, in order that a specific antioxidant composition be pharmacologically and physiologically acceptable for therapeutic use in-vivo—in addition to its ability to accumulate and concentrate within mitochondria—the medical and pharmaceutical communities have set forth a series of fundamental questions to be asked and answered during the development of a potentially efficacious antioxidant composition [see for example: Murphy M P, Targeting bioactive compounds to mitochondria, *Trends Biotechnol* 15:326-330, 1997; and Murphy M P & Smith R A J, Targeting antioxidants to mitochondria by conjugation to lipophilic cations, *Annu Rev Pharmacol Toxicol* 47:629-656, 2007].

The nature of these inquires include the following:
(i) Against what specific biological molecule or chemical entity is the antioxidant supposed to protect?
(ii) Do sufficient quantities of the antioxidant composition reach its intended target in-vivo to protect the mitochondria effectively?
(iii) In what manner does the antioxidant composition protect the mitochondria in-vivo? (i.e., is it by scavenging reactive oxygen species, "ROS"? or by preventing ROS formation? or by up-regulating defenses? or by aiding in mtDNA repair?)
(iv) If the antioxidant composition functions by scavenging ROS, can the resultant antioxidant-derived reaction products themselves cause damage to cells, or be neutralized or be recycled/regenerated?
(v) Can the antioxidants composition cause damage to other cells, tissues, organs, or systems within the living subject?

Consequently, in order to be pharmaceutically and physiologically acceptable, a newly developed antioxidant composition must present several specific attributes and properties. Among these typically are:

An acceptable oral bioavailability;

A selective uptake by mitochondria within those cells, tissues and organs most affected by mitochondrial oxidative damage;

An effective blocking of oxidative damage within mitochondria, coupled with the ability to be recycled to the active form of antioxidant within mitochondria or be removed by the systems of the living subject; and A clinically efficacious activity value for the antioxidant composition at dosage concentrations well below that threshold amount/value which will cause toxicity or other harmful side effects in-vivo.

It would also be most desirable—for long-term administration of the antioxidant composition—if the substance had a natural process of accumulation and removal in-vivo, which would limit its uptake and enabling the antioxidant concentration to come to a steady-state distribution within the living subject.

Conventionally Known Kinds of Antioxidant Compositions

A variety of different compositions have been demonstrated to have active and efficacious properties; and the majority of such compositions are antioxidants. This is not surprising, particularly in view of the fact that an antioxidant, by definition, is any chemical composition which retards or inhibits the oxidation of another substance to which it is added. Accordingly, the sources, types, and modes of activity for antioxidants are amazingly broad.

Naturally Occurring Substances

In mammals, the cellular levels of reactive oxygen species ("ROS") produced by normal mitochondrial function increase throughout the aging process [Passos et al, Mitochondria and ageing: winning and losing in the numbers game, *BioEssays* 29:908-917, 2007]. Many dietary supplements and foods are rich in natural antioxidants that demonstrably quench ROS in some degree; and these have become increasingly popular for their presumed prophylactic benefit [Kidd P M, Neurodegeneration from mitochondrial insufficiency: Nutrients, stem cells, growth factors, and prospects for brain rebuilding using integrative management, *Alt Med Rev* 10:268-293, 2005; and Bjelakovic G & Gluud C, Surviving antioxidant supplements, *J Natl Cancer Inst* 99:742-743, 2007].

However, ingesting high doses of such antioxidants does not increase bioavailability, and under certain conditions may even be toxic to the living host [Sapone et al, High-dose vitamin A, *Lancet* 370:740, 2007]. Thus, targeting a low, but therapeutic dosage of a naturally occurring antioxidant to impaired mitochondria has become an appealing approach [see for example: Liu et al, Flex-Nets differentially induce apoptosis in cancer over normal cells by directly targeting mitochondria, *Mol Cancer Ther* 6:1814-1822, 2007; Mukhopadhyay A & Weiner H, Delivery of drugs and macromolecules to mitochondria, *Adv Drug Deliv Rev* 59:729-738, 2007; and Murphy M P & Smith R A J, Targeting antioxidants to mitochondria by conjugation to lipophilic cations, *Annu Rev Pharmacol Toxicol* 47:629-656, 2007].

Some naturally occurring chemical substances—such as the retinoids, alpha-lipoic acid, and synthetic ubiquinone (coenzyme Q) analogs exemplified by idebenone—share in common intrinsic antioxidant properties that may help mitigate in-vivo damage caused to DNA by reactive oxygen species ("ROS") [Orrenius et al, Mitochondrial oxidative stress: Implications for cell death, *Annu Rev Pharmacol Toxicol* 47:143-183, 2007]. Merely as illustrative of the potential for such naturally occurring medicaments, the following examples have been considered:

(i) Idebenone is today pharmaceutically prescribed for a number of medical complaints such as chronic fatigue, ataxia, and other cognitive disorders [see for example: Rustin et al, Effect of idebenone on cardiomyopathy in Friedreich's ataxia: a preliminary study, *Lancet* 354:477-479, 1999; Kidd P M, Neurodegeneration from mitochondrial insufficiency: Nutrients, stem cells, growth factors, and prospects for brain rebuilding using integrative management, *Alt Med Rev* 10:268-293, 2005].

(ii) Palmitic acid is a major constituent of the docosahexaenoic acids used to treat breast cancer and the lipodystrophies [Nkondjock A & Ghadirian P, Intake of specific carotenoids and essential fatty acids and breast cancer risk in Montreal, Canada, *Am J Clin Nutr* 79:857-864, 2004; Listenberger et al, Triglyceride accumulation protects against fatty acid-induced lipotoxicity, *Proc Natl Acad Sci USA* 100:3077-3082, 2003].

(iii) The use of alpha-lipoic acid in cancer therapy and other clinical applications is under intensive investigation [see for example: Van de Mark et al, α-Lipoic acid induces p27$^{Kip}$-dependent cell cycle arrest in non-transformed cell lines and apoptosis in tumor cell lines, *J Cell Physiol* 194:325-340, 2003; Nichols Jr. T W, α-Lipoic acid: Biological effects and clinical implications, *Alt Med Rev* 2:177-183, 1997; Bilska A & Wtodek L, Lipoic Acid—the drug of the future?, *Pharmacol Reports* 57:570-577, 2005].

(iv) Retinoic acid is used to treat cervical and ovarian cancers [Soprano et al, Rb2/p130 and protein phosphatase 2A: key mediators of ovarian carcinoma cell growth suppression by all-trans retinoic acid, *Oncogene* 25:5315-5325, 2006].

(v) Other natural antioxidants such as resveratrol are said to stimulate mitochondrial biogenesis [Passos et al, Mitochondria and ageing: winning and losing in the numbers game, *BioEssays* 29:908-917, 2007].

(vi) Short-chain fatty acids can affect gamma globin expression [Pace et al, Short-chain fatty acid derivatives induce fetal globin expression and erythropoiesis in vivo, *Blood* 100:4640-4648, 2002].

Lipophilic Cation Conjugates

Another approach for targeting antioxidants to mitochondria has been by conjugation to a lipophilic cation, such as the triphenylphosphonium ("TPP") cation [Murphy M P, Targeting lipophylic cations to mitochondria, *Biochim Biophys Acta* 1777:1028-1031, 2008; Murphy M P & Smith R A J, Targeting antioxidants to mitochondria by conjugation to lipophilic cations, *Annu Rev Pharmacol Toxicol* 47:629-656, 2007].

By definition, a lipophilic cation is a positively charged chemical entity having a large, hydrophobic surface area that enables it to pass through the phospholipid bilayers of and to accumulate within mitochondria [Murphy M P & Smith R A J, Drug delivery to mitochondria: the key to mitochondrial medicine, *Adv Drug Deliv Rev* 41:235-250, 2000; Murphy M P, Development of lipophilic cations as therapies for disorders due to mitochondrial dysfunction, *Exp Opin Biol Ther* 1:753-764, 2001; Smith et al, Using mitochondria-targeted molecules to study mitochondrial radical production and its consequences, *Biochem Soc Trans* 31:1295-1299, 2003; Smith et al, Targeting coenzyme Q derivatives to mitochondria, *Meth Enzymol* 382:45-67, 2003; Murphy M P, Targeting bioactive compounds to mitochondria, *Trends Biotechnol* 15:326-330, 1997].

The conjugation to a lipophilic cation procedure is said to generate orally bioavailable molecules which can accumulate in the cell, are driven by the plasma membrane potential, and will concentrate within the mitochondria. Once concentrated within the mitochondria, the antioxidant-lipophilic cation conjugate moiety can protect the mitochondrial DNA (mtDNA) from oxidative damage; and after exerting its protective activity against reactive oxygen species (ROS), can often then be recycled back from the used condition into its active form.

In furtherance of this approach, a class of such mitochondria-targeted antioxidants has been developed by conjugating the lipophilic triphenylphosphonium cation to an antioxidant moiety, such as ubiquinol or α-tocopherol. As reported in the scientific literature, these compounds will pass easily through all biological membranes, including the blood-brain barrier, and enter into muscle cells; thereby reaching those tissues most commonly affected by mitochondrial oxidative damage. Furthermore, because of their positive charge, these conjugates are accumulated several-hundredfold within the mitochondria; are driven by the membrane potential; and thus will enhance the protection of mitochondria from oxidative damage by reactive oxygen species.

Cisplatin-Derivative Agents

A class of mitochondrial targeting drug agents is described by U.S. Pat. No. 6,316,652. This class of drug agents constitutes certain cisplatin derivatives called mitoplatins, and are intended to be used as antitumor agents. Mitoplatins are so named owing to their ability to target mitochondrial DNA specifically via the carnitine-acylcarnitine translocase system. The patent also describes various methods for synthesizing mitoplatins; preparing compositions of matter containing mitoplatins; and discloses methods for using the mitoplatins.

Structurally, these disclosed mitochondrial targeting drug agents will comprise at least three chemical components: (i) a metal preferably selected from the group consisting of, but not limited to, Pt, V, Mo, W, Mn, Tc, Fe, Ru, Co, Rh, Ni, Pd, Cu, Au and Zn; (ii) a chemical group which releases the metal to the intended target location and which includes, but is not limited to, halides, malonato, carboxylate, hetero atom substituted carboxylates, phosphates, sulfates, alkoxides, sulfides, selenides, phosphorous or nitrogen derivatives; and (iii) a compound which is transported through the mitochondrial membrane via the L-carnitine acylcarnitine translocase system; and includes, but is not limited to, naturally occurring L-carnitine or its analogs. The synthesized mitochondrial targeting drug agents may also optionally include a carrier ligand.

Other Substances (a) The use of vitamins C and E, and glutathione donors such as N-acetyl cysteine (NAC) as antioxidants is well documented [see for example: Ritch R, Natural compounds: evidence for a protective role in eye disease, *Can J Ophtamol* 42:425-438, 2007, and the references cited therein; Bjelakovic et al, Mortality in randomized trials of antioxidant supplements for primary and secondary prevention. Systematic review and meta-analysis, *JAMA* 297:842-857, 2007, and the references cited therein].

However, it is dubious whether a clear benefit is derived from taking vitamin supplements beyond that consumed in a normal diet [Bjelakovic G & Gluud C, Surviving antioxidant supplements, *J Natl Cancer Inst* 99:742-743, 2007; Evans J, Antioxidant supplements to prevent or slow down the progression of AMD: a systematic review and meta-analysis, *Eye* 22:751-760, 2008; Gray et al, Antioxidant vitamin supplement use and risk of dementia or Alzheimer's disease in older adults, *J Am Geriatr Soc* 56:291-295, 2008].

The disappointing results afforded by these studies contrast sharply with the excellent antioxidant activity of in-vitro assays, particularly for vitamins C and E. One major reason why taking supplements of antioxidants often fail to translate into a positive in-vivo effect is believed to be due to their poor bioavailability [Shen et al, How to understand the dichotomy of antioxidants, *Biochem Biophys Res Commun* 362:543-545, 2007].

(b) The recent use of superoxide/catalase mimetics such as the catalytic antioxidant manganese 5,10,15,20-tetrakis(4-benzoic acid) porphyrin (MnTBAP) has shown promise by increasing the lifespan of mice with oxidative stress-associated neurodegenerative disease [Melov et al, Lifespan extension and rescue of spongiform encephalopathy in superoxide dismutase 2 nullizygous mice treated with superoxide dismutase-catalase mimetics, *J Neurosci* 21:8348-8353, 2001].

At the forefront of this approach are the MitoQ class of compounds, and the recent development of a novel class of mitochondria-targeted peptide antioxidants known as the Szeto-Schiller (SS) peptides [Murphy M P & Smith R A, Targeting antioxidants to mitochondria by conjugation to lipophilic cations, *Annu Rev Pharmacol Toxicol* 47:629-656, 2007; and Szeto H H, Cell-permeable, mitochondrial-targeted, peptide antioxidants, *AAPS J* 8:E277-E283, 2006].

(c) Alpha-Lipoic acid has a demonstrable ability to act as an antioxidant in fat-soluble and water-soluble tissues, in both its oxidized and reduced forms [Winiarska et al, Lipoic acid ameliorates oxidative stress and renal injury in alloxan diabetic rabbits, *Biochim* 90:450-459, 2008]; and is also readily absorbed from an orally given dose. For these reasons also, lipoic acid has been used as a human nutritional supplement and in dietary prophylaxis and therapy [see for example U.S. Pat. Nos. 5,607,980; 5,536,645; 5,472,698; 5,326,699; and 5,292,538].

Because of these advantages and its low toxicity, alpha-lipoic acid is seen as a potentially effective therapeutic agent in clinical conditions associated with free radical damage. Furthermore, alpha-lipoic acid is believed to be an antioxidant candidate because of its specificity for free radical quenching, its metal chelating activity, its interaction with other antioxidants, and its effects on gene expression. Consequently, the clinical applications envisioned today for alpha-lipoic acid now include diabetic polyneuropathy, cataracts, glaucoma, ischemia-reperfusion injury, and *Amanita* mushroom poisoning [Koufaki et al, Synthesis of chroman analogues of lipoic acid and evaluation of their activity against reperfusion arrhythmias, *Bioorg Med Chem* 12:4835-4841, 2004; Packer et al, α-Lipoic acid as a biological antioxidant, *Free Rad Biol Med* 19:227-250, 1995; Nichols Jr. T W, α-Lipoic acid: Biological effects and clinical implications, *Alt Med Rev* 2:177-183, 1997].

In short, although there are various formulary and dietary compositions conventionally known and used for enhancing the metabolism of naturally occurring L-carnitine; as well as multiple examples of lipid esters of naturally occurring carnitine which function in the delivery of pharmacologically active compounds, there nevertheless remains a well-recognized and long-standing need for specific mitochondria-targeting chemical entities which will pass through the mitochondrial membranes to deliver and make available pharmacologically active compounds such as antioxidants within the interior of mitochondria harbored in a living cell. Were such a class of chemical compositions to be developed, they would represent and be unique and unforeseen innovations by ordinary practitioners now working in this technical field.

SUMMARY OF THE INVENTION

The present invention has not less than four different aspects.

A first aspect is a carrier molecule suitable for reversibly attaching and transporting an antioxidant across an intracellular membrane of mitochondria within a living cell, said carrier molecule comprising:

a carnitinoid analog composition which
  (i) is a biocompatible chemical structure which does not exist in nature,
  (ii) is comprised of three to seven carbon atoms,
  (iii) presents and maintains the stereochemistry of at least one hydroxyl group similar to that of the beta-hydroxyl group in natural L-carnitine for on-demand reaction with and reversible attachment to a biologically active antioxidant,
  (iv) is a chiral and non-racemic synthetic composition,
  (v) includes a functional group presented either as a carboxylic acid; or as an ester, an alcohol, or an ether with an aliphatic moiety or an aromatic moiety or a combination of both, and
  (vi) optionally presents at least one other hydroxyl group available for on-demand reaction with and reversible attachment to another biologically active antioxidant.

A second aspect provides a coupled carrier complex able to transport and release a reversibly attached antioxidant into the interior of mitochondria within a living cell, said coupled carrier complex comprising:

a carrier molecule for the reversible attachment and release of an antioxidant which
(i) is a biocompatible carnitinoid analog structure which does not exist in nature,
(ii) is comprised of three to seven carbon atoms,
(iii) presents and maintains the stereochemistry of at least one hydroxyl group similar to that of the beta-hydroxyl group in natural L-carnitine for on-demand reaction with and reversible attachment to a biologically active antioxidant,
(iv) is a chiral and non-racemic synthetic composition,
(v) includes a functional group presented either as a carboxylic acid; or as an ester, an alcohol, or an ether with an aliphatic moiety or an aromatic moiety or a combination of both, and
(vi) optionally presents at least one other hydroxyl group available for on-demand reaction with and reversible attachment to another biologically active antioxidant; and
an antioxidant which has reacted with and become reversibly attached to an available hydroxyl group of said carnitinoid analog composition to form a coupled carrier complex.

A third aspect defines a method for treating the mitochondria of a living cell, said method comprising the steps of:
obtaining a coupled antioxidant-carrier complex which is comprised of a carrier molecule which
(i) is a biocompatible carnitinoid analog composition which does not exist in nature,
(ii) has a carnitinoid analog structure comprising three to seven carbon atoms,
(iii) presents and maintains the stereochemistry of at least one hydroxyl group similar to that of the beta-hydroxyl group in natural L-carnitine for on-demand reaction with and reversible attachment to a biologically active antioxidant,
(iv) is a chiral and non-racemic synthetic composition,
(v) includes a functional group presented either as a carboxylic acid; or as an ester, an alcohol, or an ether with an aliphatic moiety or an aromatic moiety, or a combination of both, and
(vi) optionally presents at least one other hydroxyl group available for on-demand reaction with and reversible attachment of another biologically active antioxidant;
and an antioxidant which has reacted with and become reversibly attached to at least one available hydroxyl group to yield said coupled antioxidant-carrier complex;
introducing said coupled antioxidant-carrier complex to a living cell;
permitting said introduced coupled antioxidant-carrier complex to target and become localized within the mitochondria of the living cell; and
allowing said localized coupled antioxidant-carrier complex to release the antioxidant within the mitochondria for reaction with such reactive oxygen species as may then be present.

A fourth aspect offers a system for targeted delivery of an antioxidant into the mitochondria of a living cell comprising:
a coupled antioxidant-carrier complex comprised of
a carrier molecule for the reversible attachment and release of an antioxidant which
(i) is a biocompatible carnitinoid analog structure which does not exist in nature,
(ii) is comprised of three to seven carbon atoms,
(iii) presents and maintains the stereochemistry of at least one hydroxyl group similar to that of the beta-hydroxyl group in natural L-carnitine for on-demand reaction with and reversible attachment to a biologically active antioxidant,
(iv) is a chiral and non-racemic synthetic composition,
(v) includes a functional group presented either as a carboxylic acid; or as an ester, an alcohol, or an ether with an aliphatic moiety or an aromatic moiety or a combination of both, and
(vi) optionally presents at least one other hydroxyl group available for on-demand reaction with and reversible attachment to another biologically active antioxidant, and
an antioxidant which has reacted with and become reversibly attached to an available hydroxyl group of said carnitinoid analog composition to form a coupled carrier complex; and
means for introducing said coupled antioxidant-carrier complex to a living cell whereby said introduced coupled antioxidant-carrier complex targets and become localized within the mitochondria of the living cell, and whereby said antioxidant becomes released within the mitochondria for reaction with such reactive oxygen species as may then be present.

BRIEF DESCRIPTION OF THE FIGURES

The present invention may be more easily understood and better appreciated when considered with the accompanying Drawing, in which:

Prior Art

FIG. 3 illustrates the stereochemical structural formulas of synthesized compounds 1-6 respectively;

FIG. 4 illustrates the stereochemical structural formulas of synthesized compounds 7-10 respectively;

DETAILED DESCRIPTION OF THE INVENTION

Figure 1:
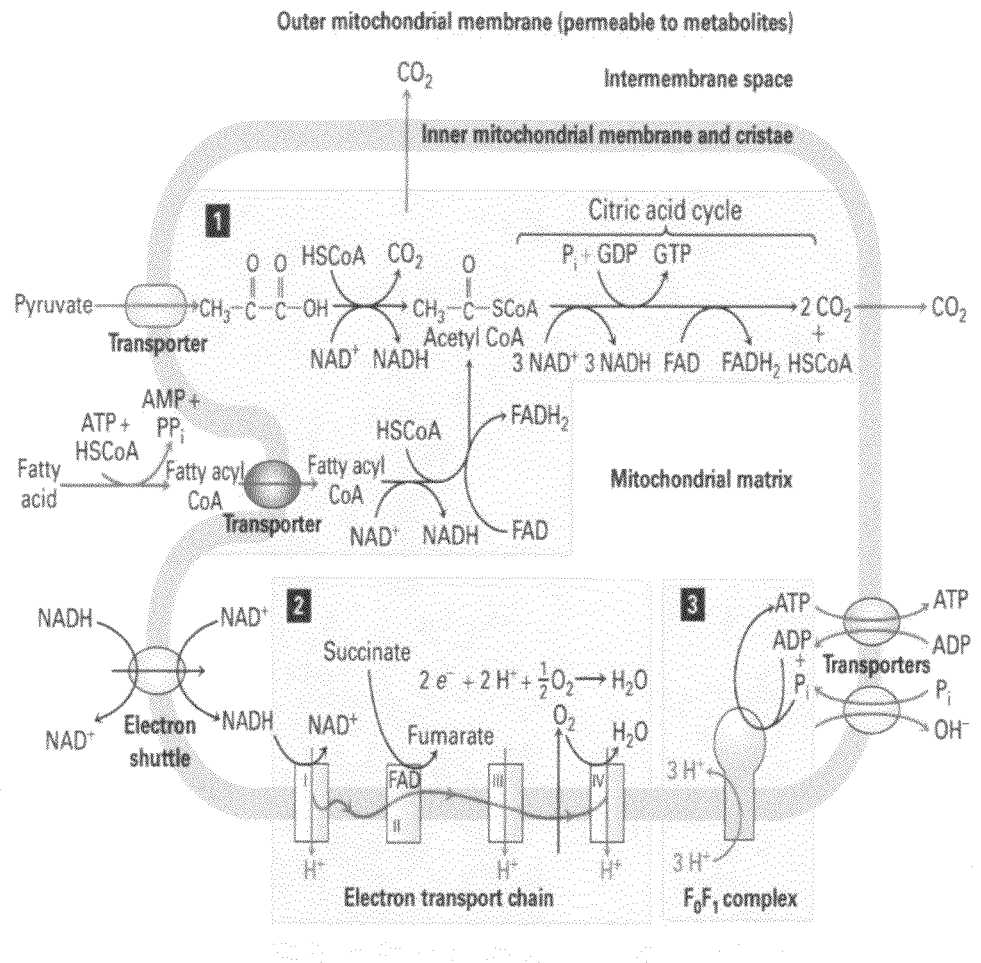
FIG. 1 presents a summary of the normal aerobic oxidation processes occurring within mitochondria.

The present invention is unique in that the subject matter as a whole has not less than four aspects: A class of chiral non-racemic carnitinoid analog carrier molecules; the subsequently formed, mitochondria-targeting, coupled antioxidant-carrier complexes; a method for introducing a pre-chosen antioxidant to the mitochondria of a living cell; and a system for delivering a pre-chosen antioxidant to the interior matrix of mitochondria within a living cell.

Each of these aspects is intimately related to all the others; and thus constitute commonly shared individual components and particular features of the unitary subject matter as a whole.

I. The Underpinnings of the Present Invention

1. Each mitochondrion in a cell has the capacity to combine oxygen with the food we eat to produce energy-yielding molecules like ATP, GTP, NADH, and FADH$_2$. But, in addition to being cellular power plants, mitochondria are also versatile and prodigious chemical factories. They produce chemical building blocks (acetyl CoA, NADH, heme, hemoglobin, nucleotide bases, amino acids, and steroids, among a long list of others) required for biosynthesis. However, the mitochondria also manufacture important signaling molecules—such as NO; reactive oxygen species ("ROS"); and cytochrome c, which acts as a signal transducing molecule when released into the cytosol and prompts the cell to undertake specific activities and/or commit suicide (apoptosis). Thus, not surprisingly, defective cells and tumor cells overtly suppress normal mitochondrial oxidative activity.

2. Small molecules, like dichloroacetate (hereinafter "DCA"), help drive the oxidation of glucose to completion by inhibiting those enzymes that restrain the uptake of pyruvate from the cytosol into the mitochondrial matrix. For this reason, DCA is today used to help treat the stroke-like episodes people afflicted with MELAS disease routinely experience. It is also being evaluated for the treatment of cancer [Bonnet et al, A mitochondria-K$^+$ channel axis is suppressed in cancer and its normalization promotes apoptosis and inhibits cancer growth, *Cancer Cell* 11:37-51, 2007].

Unfortunately, however, DCA is taken up by the mitochondria of both normal and abnormal cells; and once located within the mitochondrial membranes is routinely metabolized by the mitochondria into oxalic acid—a substance that, like lactic acid, is toxic to cells, particularly to neurons [Aicher et al, Triterpene and diterpene inhibitors of pyruvate dehydrogenase kinase (PDK), *Bioorg Med Chem Lett* 9:2223-2228, 1999].

3. In tumor cells, the complete oxidation of glucose (as pyruvate present within the mitochondria) is inhibited and energy production relies on cytoplasmic glycolysis (the Warburg effect described above). This suppressed oxidation activity by the tumor cell's mitochondria concomitantly induces a state of apoptosis resistance.

Alpha-Lipoic acid stimulates the natural uptake of pyruvate from the cytosol into the mitochondrial matrix and is part of the pyruvate dehydrogenase complex that drives the citric acid cycle. It is an essential cofactor in metabolism; and neither it nor its principal metabolic end-product [(R)-4,6-bis (methylthio)hexanoic acid] is toxic to normal cells, even when substantial amounts (up to 600 mg/day) of alpha-lipoic acid supplements are purposefully added to the diet. Studies also consistently show that the addition of alpha-lipoic acid to tumor cell lines overcomes resistance and directly induces apoptosis [see for example, Van de Mark et al, α-Lipoic acid induces p27$^{Kip}$-dependent cell cycle arrest in non-transformed cell lines and apoptosis in tumor cell lines, *J Cell Physiol* 194:325-340, 2003].

However, the bioavailability of alpha-lipoic acid in humans, whether obtained from food sources, or by oral supplements, or via parenteral means, is very short-lived. Alpha-Lipoic acid is found to concentrate highest in the liver and only minor amounts will enter the blood circulation from food or biosynthesis. In particular, the plasma half-life of alpha-lipoic acid is less than 1 hour; after which it is excreted, mainly in the urine, within 24 hours [Hermann et al, Enantioselective pharmacokinetics and bioavailability of α-lipoic acid formulations in healthy volunteers, *Eur J Pharma Sci* 4:167-174, 1996; Teichert J & Preis R, High-performance liquid chromatographic assay for α-lipoic acid and five of its metabolites in human plasma and urine, *J Chromatogr B* 769:269-281, 2002].

4. Other natural products such as the retinoids, as well as some synthetic ubiquinone (coenzyme Q) analogs such as idebenone, individually demonstrate intrinsic antioxidant properties that help mitigate in-vivo damage to cellular DNA caused by reactive oxygen species or "ROS" [Orrenius et al, Mitochondrial oxidative stress: Implications for cell death, *Annu Rev Pharmacol Toxicol* 47:143-183, 2007].

In mammals, the cellular levels of ROS (produced by normal mitochondrial function) typically increase throughout the aging process, an effect leading at least in part to the markedly reduced respiration capacity commonly seen in geriatric persons. Nevertheless, while dietary supplements and foods rich in antioxidants that quench ROS have become popular for their presumed prophylactic benefit, it is now recognized that ingesting high doses of antioxidants does not increase their bioavailability internally and, in certain instances, may even be toxic [Passos et al, Mitochondria and ageing: winning and losing in the numbers game, *BioEssays* 29:908-917, 2007; Bjelakovic G & Gluud C, Surviving antioxidant supplements, *J Natl Cancer Inst* 99:742-743, 2007; Sapone et al, High-dose vitamin A, *Lancet* 370:740, 2007; de Oliveira M R & Moreira J C F, Acute and chronic vitamin A supplementation at therapeutic doses induces oxidative stress in submitochondrial particles isolated from cerebral cortex and cerebellum of adult rats, *Toxicol Lett* 173:145-150, 2007; Kidd P M, Neurodegeneration from mitochondrial insufficiency: Nutrients, stem cells, growth factors, and prospects for brain rebuilding using integrative management, *Alt Med Rev* 10:268-293, 2005].

Based on all the foregoing, the essential premises and fundamental underpinnings of the present invention become recognized, focused and clearly understood. These underpinnings therefore are:

(i) If one wishes to deliver pharmacologically meaningful concentrations of antioxidant compositions to achieve therapeutic purposes, then the manner of delivery must be specifically targeted to specified locations or organelles within the living cell.

(ii) The most desirable mode for the delivery of therapeutically meaningful concentrations of antioxidant compositions is to engage the living body's own natural systems as a mechanism for purposefully targeting a prepared antioxidant composition into the mitochondrial inner matrix.

(iii) The most advantageous technique would be if the chosen antioxidant and the means for its delivery to the living cell utilized those in-vivo mechanisms employed by naturally occurring compounds found in the living body.

(iv) The methodology would most benefit from a synthesized substance, which when metabolized by the body, will generate metabolic break-down products in-vivo which have little or no demonstrated potential for toxicity or for causing harmful side effects within the living host.

(v) The compositions and the methodology would be broadly operative, efficacious, and beneficial for mitochondrial-associated diseases and disorders generally; and such treatments would be equally effective for therapeutically treating impaired or damaged mitochondria then existing within the living cells of solid tumors and clinical cancers.

II. Definitions

In order to avoid inconsistencies in terminology, to eliminate ambiguities in denotative and connotative meanings, and to increase the clarity and completeness of comprehension and understanding, a set of terms and definitions is presented below. The terms and jargon defined below will be employed consistently and repeatedly herein to describe accurately and to claim precisely what constitutes the present invention in a manner that not only sets forth what the present invention is and how it is to be made and used, but also separates and distinguishes the inventive subject matter from what it is not.

Carrier: a molecule to which a substance may be reversibly attached for transport to a particular site or location, typically across an intracellular membrane, and which is then released locally.

Carnitinoid: a compound related to the chemical formulation and structure of carnitine.

Acyclic carnitinoid: an open, linear, or branched carbon-chain compound which contains a segment related to the formulation and structure of carnitine within its stereochemical framework.

Cyclic carnitinoid: a closed-chain or ring-containing compound which contains a segment related to the formulation and structure of carnitine within its stereochemical ring framework.

Glycocarnitinoid: a modified (monosaccharide) sugar compound that contains a segment within its core stereochemical framework which is related in some degree to the formulation and structure of carnitine.

Chiral: a molecule or compound that cannot be superimposed on its mirror image forms (i.e., isomers or enantiomers); and the mirror image structures are distinguished by their chirality or right/left handedness of their stereochemistries.

Non-racemic: a composition which is a single enantiomer or isomeric form of a substance which exists in a pure or crystalline form; and is distinguished from a racemic mixture composed of two or more enantiomorphic isomers, which is optically inactive.

Anomer: the alpha or beta form of a sugar produced when the possibility of stereoisomerism is available to the carbonyl carbon atom by the formation of an oxygen-containing ring.

Analog or analogous structure: a compound with a structure similar to that of another but differing from it in respect to a certain component.

Homolog or homologous series: a compound or series of compounds each of which is formed from the one before it by the insertion of a methylene "$CH_2$" group in the molecule.

Linking molecule: a difunctional group-containing molecule known to one ordinarily skilled in the art of chemical synthesis that can be used to connect two compounds together by forming covalent bonds between one of its functional groups (i.e., a carboxylic acid) and a complimentary functional group in one compound (i.e., an alcohol) and between the other of its functional groups and a complimentary functional group in the other compound.

Zwitterion: an ion that has both positive and negative regions of charge.

Inner salt: a zwitterion.

Stem cells: unspecialized cells that can self-renew indefinitely and that can also differentiate into more mature cells with specialized functions.

Embryonic stem cells: primitive (undifferentiated) cells from the embryo that have the potential to become a wide variety of specialized cell types.

Differentiation: the process whereby an unspecialized early embryonic cell acquires the features of a specialized cell such as a heart, liver, or muscle cell.

Acyl group: a radical formed by removing a hydroxyl group from an organic acid, wherein RCO— is the general formula and R may be an aliphatic, alicyclic, or aromatic moiety.

Antioxidant: a substance that retards or inhibits the oxidation of another substance to which it is added.

Disorder: a derangement or abnormality of function; typically a morbid physical or mental state.

Disease: a well-delineated disorder of the structure or functions of a living organism which has a predictable progression or course of events sequence.

III. The Chemical Class of Synthetic Carnitinoid Analog Carriers

The present invention relies upon and requires the use of chiral, non-racemic, synthetic carnitinoid analog compositions as a unique class of functional biochemical carriers. Accordingly, each embodiment of the synthesized carrier compounds is a functional conveyor or transporter molecule which is operative under ex-vivo, in-vitro, and in-vivo circumstances; is a conveyor molecule to which another discrete compound or substance may be chemically attached; is a porter molecule by which the attached substance is transported across an intracellular membrane of mitochondria; and is a delivery molecule by which a substance is reversibly attached and then made available for subsequent reaction within the mitochondria after having been passed through the intracellular membrane.

Accordingly, each embodiment of the carrier compounds is a chiral composition—i.e., a molecule that cannot be superimposed on its mirror image forms (i.e., isomers or enantiomers); and the mirror image structures are distinguished by their chirality or right/left handedness of their stereochemistries. Similarly, each embodiment of the carrier compounds is a non-racemic composition—i.e., a single enantiomer or isomeric form of a substance which exists in a pure or crystalline form; and can be distinguished from a racemic mixture composed of two or more enantiomorphic isomers, which is optically inactive.

The functional biochemical carriers of the present invention constitute a chemical class of purposefully prepared synthetic compounds which can be introduced to a living cell; are able specifically to target and localize within the mitochondria then present within a living cell; are individually and can collectively serve as molecular porters or transporters of prechosen medicaments, such as an antioxidant; and are useful for the repair of impaired or damaged mitochondria as well as for the therapeutic treatment of mitochondrial-associated diseases and disorders in a living mammal.

The Membership of the Class

The members constituting this unique class of functional biochemical carrier molecules all share a number of particular structural traits, specific substantive attributes, and minimal stereochemical requirements. Accordingly, each member of the class and every embodiment of the invention exhibit the following characteristics and properties:

(i) Each is a carnitinoid analog composition.

(ii) Each has a biocompatible chemical structure which does not exist in nature. Each carrier molecule thus is a biocompatible analog of L-carnitine and is an artificially prepared compound which must be chemically synthesized by a chemist.

(iii) Each is a chiral, non-racemic synthetic composition;

(iv) Each has a chemical structure comprised of not less than three and not more than seven carbon atoms.

(v) Each presents at least one hydroxyl group (normally the second or beta carbon from the carboxylate carbon or, if the carboxylate is in the reduced functional form, the primary hydroxyl group of the structure), and maintains the stereochemistry of the available hydroxyl group similar to that of the beta or "β"-hydroxyl group as it appears within natural L-carnitine, for on-demand reaction with and reversible attachment of a biologically active antioxidant.

By this requirement, each carrier molecule will present at least one (and preferably two or more) discrete hydroxyl groups for reaction; and, while each stereocenter in the molecule may adopt either an R or S relative configuration, the enantiopure form of the carrier is a structure which will maintain the absolute stereochemistry of the beta or "β"-hydroxyl group similar to its existence within natural L-carnitine.

This latter requirement is illustrated by the structural representation appearing below.

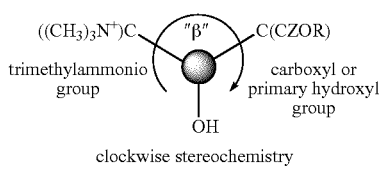

clockwise stereochemistry

Thus, when looking down the C—H axis of the carbon stereocenter to which the "β"-hydroxyl group is attached (such that the hydrogen atom is placed away from the observer), the three remaining substituents—the hydroxyl group, the carbon atom to which the quaternary nitrogen is attached, and the carbon atom to which the CZOR (carboxyl or primary hydroxyl) group is attached—follow a clockwise pattern.

(vi) Each member and embodiment allows for the direct reversible attachment of at least one molecule (and desirably two or more molecules) of an antioxidant composition via a covalent bond linkage.

(vii) Each member and embodiment of the chemical class, with or without an attached antioxidant composition, will specifically target and localize within the mitochondria of a living cell; and will pass freely from the cytoplasm through the outer and inner membranes of mitochondria, and then back again into the cytoplasm repeatedly.

(viii) Each member and embodiment of the chemical class will include a functional group presented either as a carboxylic acid; or as an ester, an alcohol, or an ether with an aliphatic moiety or an aromatic moiety or a combination of both.

(ix) Each member and embodiment of the chemical class will optionally, but preferably, present at least one other hydroxyl group available for on-demand reversible attachment to a biologically active antioxidant.

Three Different Subset Groupings Constituting a Single Chemical Class

Within this singular chemical class, three distinctly different, but intimately related, structural subsets or formulated groupings of carnitinoid analog carriers predominant. These are: the acyclic (alkyl) carnitinoid analogs; the cycloalkyl carnitinoid analogs; and the glycocarnitinoid analogs. Cumulatively and collectively, these three individual chemical subdivisions offer a broad range and a wide variety of biologically compatible, carnitinoid analog carriers suitable for use in-vivo with mitochondrial associated pathologies.

A. The Acyclic (Alkyl) Carnitinoid Analog Carriers

This first discrete subset of analogs comprises those analog compositions and formulated structures that are chemically substituted and derivatized forms of natural carnitine [(2R)-3-carboxy-2-hydroxy-N,N,N-trimethyl-1-propanaminium inner salt]. The chemical formulation and general structure of these substituted carnitine analogs are shown by Structural Formula A1 below.

The 4-Carbon Format

Structural Formula A1:

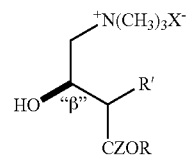

wherein X is a halogen atom or a pharmaceutically acceptable anion [some non-limiting examples of pharmaceutically acceptable anions are listed in: Paulekuhn et al, Trends in active pharmaceutical ingredient salt selection based on analysis of the Orange Book database, *J Med Chem* 50:6665-6672, 2007];

wherein Z either is an oxygen atom or two hydrogen atoms;
wherein R is a lone-pair of electrons (zwitterion); or is a hydrogen atom; or is an aliphatic moiety or an aromatic moiety, or a combination of both; and
wherein R' either is a hydrogen atom or a hydroxyl group.

Thus, by Structural Formula A1 above, the "CZOR" entity is a functional group presented either as a carboxylic acid; or as an ester, an alcohol, or an ether with an aliphatic moiety or an aromatic moiety or a combination of both.

In its preferred formats, when X is a halogen, it either is a chlorine or a bromine atom;
Z is an oxygen atom; and
R desirably is a hydrogen atom; or is an ethyl or methyl group; or is a benzyl or 4-methoxybenzyl group.

In addition, carnitinoid homologs similar to Structural Formula A1, but presenting a 5-carbon or 6-carbon-chain backbone (rather than a four carbon-chain structure) are also suitable. Illustrations of these alternative and additional formats are presented by Structural Formulas A2-A6 respectively, as shown below.

The 5-Carbon Formats

Structural Formula A2:

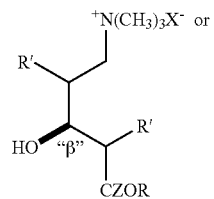

Structural Formula A3:

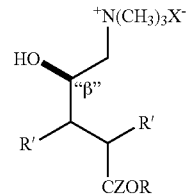

The 6-Carbon Formats

Structural Formula A4:

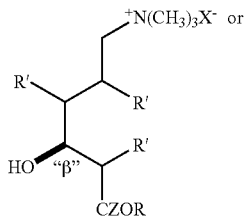

Structural Formula A5:

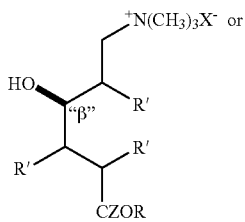

Structural Formula A6:

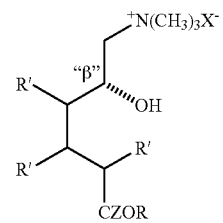

In each of Structural Formulas A2-A6 respectively, X is a halogen atom or any other pharmaceutically acceptable anion;

Z either is an oxygen atom or two hydrogen atoms;

R is a lone-pair of electrons (zwitterion); or is a hydrogen atom; or is an aliphatic moiety or an aromatic moiety, or a combination of both; and each R' independently either is a hydrogen atom or a hydroxyl group.

Thus, by Structural Formulas A2-A6 above, the "CZOR" entity is a functional group presented either as a carboxylic acid; or as an ester, an alcohol, or an ether with an aliphatic moiety or an aromatic moiety or a combination of both.

In addition, while each stereocenter in the molecule presented by Structural Formulas A1-A5 may adopt either an R or S relative configuration, the enantiopure form of the carrier molecule is a structure which will maintain the absolute stereochemistry of one hydroxyl group similar to the beta or "β"-hydroxyl group as it exists within natural L-carnitine. This type of positioning is illustrated by the following representation.

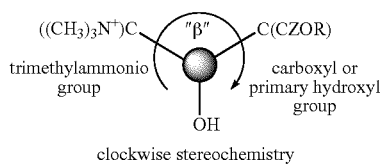

clockwise stereochemistry

Accordingly, when looking down the C—H axis of the stereocenter to which the "β"-hydroxyl group is attached (such that the hydrogen atom is placed away from the observer), the three remaining substituents—i.e., the hydroxyl group, the carbon atom to which the quaternary nitrogen is attached, and the carbon atom to which the CZOR (carboxyl or primary hydroxyl) group is attached—follow a clockwise pattern.

The synthesis of the different analog structures illustrated by Structural Formulas A1-A6 respectively is deemed to be common and ordinary knowledge long available to the ordinarily skilled organic chemist [see for example: Enomoto et al, Molecular identification of a novel carnitine transporter specific to human testis. Insights into the mechanism of carnitine recognition, *J Biol Chem* 277:36262-36271, 2002; and Degenhardt C R, Synthesis of carnitine homologues. Reactions of tertiary amines with epoxy esters, *J Org Chem* 45:2763-2766, 1980].

B. The Cycloalkyl Carnitinoid Analogs

This second discrete subset grouping of carnitinoid analogs comprises those analog compositions and formulated structures that are cycloalkyl structures in which a segment or portion of the formulation is related in some degree or manner to the naturally occurring linear carnitine molecule. The synthesis of these chemical formats is deemed to be common and ordinary knowledge long available to the ordinarily skilled organic chemist.

As merely one representative example and illustration, the chemical formulation and general structure of the cyclohexyl-based analogs will conform to Structural Formula B1 as presented below.

Structural Formula B1:

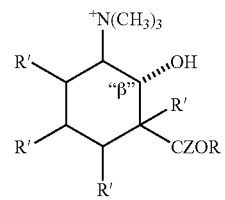

wherein Z either is an oxygen atom or two hydrogen atoms;

R is a lone-pair of electrons (zwitterion); or is a hydrogen atom; or is an aliphatic moiety or an aromatic moiety or a combination of both; and each R' independently either is a hydrogen atom or a hydroxyl group.

Thus, by Structural Formula B1 above, the "CZOR" entity is a functional group presented either as a carboxylic acid; or as an ester, an alcohol, or an ether with an aliphatic moiety or an aromatic moiety or a combination of both.

In addition, cycloalkyl homologs similar to Structural Formula B1, but presenting a 3-, 4-, 5-, or 7-carbon ring (rather than a cyclohexyl ring) format are also suitable. Illustrations of these additional formats are illustrated by Structural Formulas B2 through B5 respectively, as shown below.

Structural Formula B2:

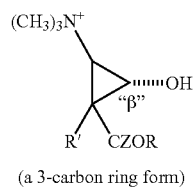

(a 3-carbon ring form)

Structural Formula B3:

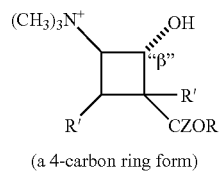

(a 4-carbon ring form)

Structural Formula B4:

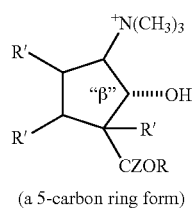

(a 5-carbon ring form)

Structural Formula B5:

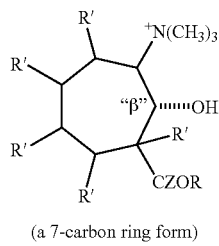

(a 7-carbon ring form)

wherein Z either is an oxygen atom or two hydrogen atoms;

wherein R is a lone-pair of electrons (zwitterion); or is a hydrogen atom; or is an aliphatic moiety or an aromatic moiety, or a combination of both; and wherein each R' independently either is a hydrogen atom or a hydroxyl group.

Thus, by Structural Formulas B2-B5 above, the "CZOR" entity is a functional group presented either as a carboxylic acid; or as an ester, an alcohol, or an ether with an aliphatic moiety or an aromatic moiety or a combination of both.

In addition, while each stereocenter in the molecule presented by Structural Formula B1-B5 may adopt either an R or S relative configuration, the enantiopure form of the carrier molecule is a structure which will maintain the absolute stereochemistry of one hydroxyl group similar to the beta or "β"-hydroxyl group as it exists within natural L-carnitine. This type of positioning is illustrated by the following representation.

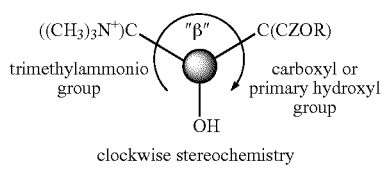

clockwise stereochemistry

Accordingly, when looking down the C—H axis of the stereocenter to which the "β"-hydroxyl group is attached (such that the hydrogen atom is placed away from the observer), the three remaining substituents—i.e., the hydroxyl group, the carbon atom to which the quaternary nitrogen is attached, and the carbon atom to which the CZOR (carboxyl or primary hydroxyl) group is attached—follow a clockwise pattern.

C. The Glycocarnitinoid Analogs

This third discrete subset of analogs comprises those carnitinoid analog compositions and formulated structures which are derivatives of a modified five or six carbon sugar (monosaccharide) that contains a segment within its core stereochemical framework and which is related in some degree to the formulation and structure of carnitine.

The modified five and six carbon sugars containing the carnitinoid segment may occur in any of their pyranose or furanose cyclic structures; in either their aldonolactone or aldarolactone forms; or as open-chain aldose/ketose, aldonic or aldaric substituted and/or derivatized formulations, which mimic or resemble in part the naturally occurring linear carnitine structure. The chemical synthesis of all such five and six carbon monosaccharide glycocarnitinoids is deemed to be ordinary knowledge available to the ordinarily skilled organic synthesis chemist.

For the sake of descriptive completeness, the five and six carbon sugars will include: The pentose monosaccharides such as ribose, ribulose, arabinose, xylose, xylulose, and lyxose; and the hexose monosaccharides such as allose, psicose, altrose, glucose, fructose, mannose, gulose, sorbose, iodose, galactose, tagatose, and talose.

In many of the most preferred embodiments, the chemical formulation and general structure of these analogous forms are 6-carbon sugar analogs, which are generally encompassed and represented by: aldopyranose Structural Formula C1 for an aldohexose derivative; and ketopyranose Structural Formula C2 for a ketohexose derivative, as shown below;

Structural Formula C1:

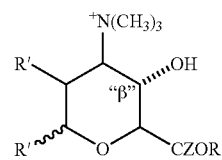

Structural Formula C2:

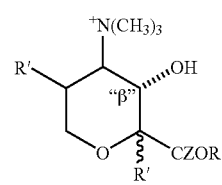

as well as ketohexose analogs, which are generally encompassed and represented by ketofuranose Structural Formulas C3 and C4, as shown below;

Structural Formula C3:

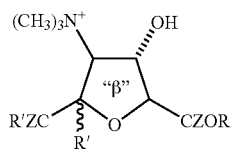

Structural Formula C4:

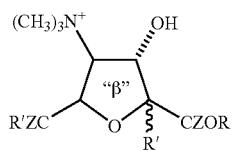

Open-chain 6-carbon sugar analogs—which are generally encompassed and represented by Structural Formula C5 for an aldohexose derivative, and by Structural Formulas C6 and C7 for a ketohexose derivative, as shown below—are also suitable;

Structural Formula C5:

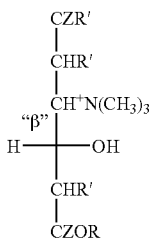

Structural Formula C6:

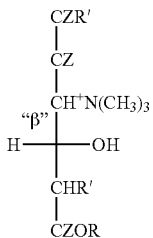

Structural Formula C7:

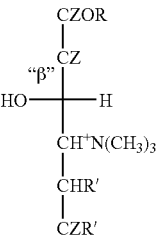

It will also be recognized and appreciated that the stereochemical structure of Structural Formulas C1-C7 can include and be based upon any isomeric form of a six carbon sugar. Thus, the analog chemical structure may be based on any of the natural hexose/ketose sugars (including D-allose, D-psicose, D-altrose, D-mannose, D-gulose, D-sorbose, D-idose, D-galactose, D-talose, D-tagatose, D-fructose), as well as upon D-glucose.

In addition, monosaccharide-based analogs having an open-chain aldose/ketose, aldonic or aldaric derivatized form—or a cyclic aldonolactone and aldarolactone form similar to aldo/ketohexose-derived analogs, but presenting a 5-carbon structural format (a pentose such as D-ribose, D-ribulose, D-arabinose, D-xylose, D-xylulose, and D-lyxos) as represented by aldofuranose Structural Formula C8 and open-chain Structural Formula C9 for aldopentose derivatives, and by Structural Formula C10 for ketopentose derivatives, as shown below, rather than a 6-carbon structural format, are also very suitable;

Structural Formula C8:

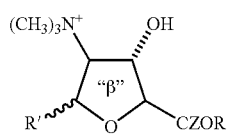

Structural Formula C9:

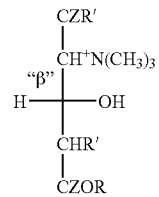

Structural Formula C10:

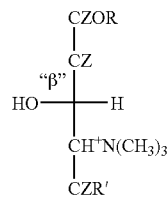

wherein for each of Structural Formulas C1-C10, each Z independently either is an oxygen atom or two hydrogen atoms;

R is a lone-pair of electrons (zwitterion); or is a hydrogen atom; or is an aliphatic moiety or an aromatic moiety, or a combination of both; and each R' independently either is a hydrogen atom or a hydroxyl group.

Thus, by Structural Formulas C1-C10 above, the "CZOR" entity is a functional group presented either as a carboxylic acid; or as an ester, an alcohol, or an ether with an aliphatic moiety or an aromatic moiety or a combination of both.

Similarly, while each stereocenter in the molecule illustrated by Structural Formulas C1-C10 may adopt either an R or S relative configuration, the enantiopure form of the carrier molecule is a structure which will maintain the absolute stereochemistry of the beta or "β"-hydroxyl group in a manner similar to that existing in natural L-carnitine. This distinguishing stereochemistry is illustrated by the following representation.

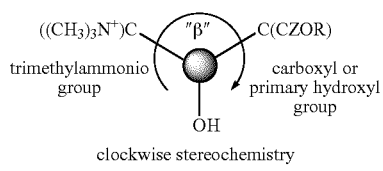

clockwise stereochemistry

Thus, when looking down the C—H axis of the carbon stereocenter to which the "β"-hydroxyl group is attached, so that the hydrogen atom is placed away from the observer, the three remaining substituents—i.e., the hydroxyl group, the carbon atom to which the quaternary nitrogen is attached and the carbon atom to which the CZOR (carboxyl or primary hydroxyl) group is attached—stereochemically follow a clockwise pattern. The anomeric hydroxyl group (or substituted derivative) may adopt either the alpha or beta anomeric forms.

IV. Suitable Antioxidant Compositions

For purposes of the present invention, it is preferred that the chosen antioxidant be a substance which has particular traits and demonstrable characteristics:

(a) The antioxidant composition will most often exist and be typically known as a naturally occurring substance which is typically present as a composition within the body of a normal living mammal. In addition, however, a variety of chemically synthesized antioxidants may also be usefully employed whenever needed or desired.

(b) The antioxidant composition will provide a chemical formulation and structure that allows it to react (directly or through a linking molecule) with at least the beta or "β"-hydroxyl group (and also preferably with additional hydroxyl groups), and thereby become reversibly attached to the carrier molecule via a covalent bond linkage.

(c) The antioxidant composition will typically have well recognized and demonstrable biological properties against such reactive oxygen species as are to be found within the interior of mitochondria of a living cell.

(d) The antioxidant composition will be pharmacologically active and retain its characteristic biological properties while in a reversibly attached (covalently bound) state as it would in its freely mobile form.

(e) The antioxidant composition will most often exist as a naturally occurring substance and include those typically to be found in edible foodstuffs such as fish, meat, nuts, seeds, fruits, legumes, herbs, spices, and tubers; or in liquids such as cocoa, coffee, tea, beer, or wine normally consumed.

(f) The antioxidant composition may be a surrogate compound, or a synthetic substitute, or a precursor form of a naturally occurring substance. These antioxidants will typically have demonstrable antitumor properties.

Accordingly, among the conventionally known antioxidant compositions which satisfy this criteria are those naturally occurring fatty acids which exist in abundance within the living mammalian body, as are exemplified by palmitic acid and their corresponding fatty acyl groups. These organic fatty acids are individually and severally very desirable for use as antioxidant compositions.

In addition, there are many other kinds of compositions and substances which also demonstrably have the requisite intrinsic antioxidant properties and meet the essential criteria listed above. Merely representative and illustrative of such naturally occurring antioxidants are the particular examples given by Table 1 below.

TABLE 1

| Desirable Antioxidant Compositions | | |
| --- | --- | --- |
| Organic Acids | | |
| carbonic acid | myristic acid | dihydrolipoic acid |
| formic acid | pentadecanoic acid | cysteine |
| acetic acid | palmitic acid | methionine |
| dichloroacetic acid | margaric acid | KAPA |
| propanoic acid | stearic acid | DAPA |
| butanoic acid | nonadecanoic acid | caffeic acid |
| valeric acid | linolenoic acid | coumaric acid |
| caproic acid | stearidonic acid | chlorogenic acid |
| caprylic acid | eicosapentaenoic acid | vanillic acid |
| octanoic acid | linoleic acid | ferulic acid |
| nonanoic acid | palmitoleic acid | nicotinic acid |
| capric acid | oleic acid | maleic acid |
| undecanoic acid | arachidonic acid | fumaric acid |
| lauric acid | pantothenic acid | succinic acid |
| tridecanoic acid | alpha-lipoic acid | adipic acid |
| Coenzyme Qs | Vitamins | Phenols |
| ubiquinone | vitamin A (A1-A3, retinoids, carotenoids) | flavonoids |
| ubiquinol | vitamin C (ascorbic acid) | resveratrol |
| idebenone | vitamin D (D1-D7) | epigallocatechin |
| plastoquinone | vitamin E (trolox) | epigallocatechin-3-gallate |
| | vitamin G | genistein |
| | vitamin H (biotin) | curcumin |
| | vitamin I | delphinidin |
| | vitamin K | |
| | vitamin M | |
| | vitamin Q | |
| | vitamin U | |

As an intrinsic part of the multiple choices listed by Table 1 above, the following is presented:

(¶) The short, medium, and long-chain fatty acids will include carbonic acid, formic acid, acetic acid, dichloroacetic acid, propanoic acid, butanoic acid, valeric acid, caproic acid, caprylic acid, octanoic acid, nonanoic acid, capric acid, undecanoic acid, lauric acid, tridecanoic acid, myristic acid, pentadecanoic acid, palmitic acid (hexadecanoic acid), margaric acid, stearic acid, nonadecanoic acid, linolenoic acid (omega 3), stearidonic acid (omega 4), eicosapentaenoic acid (omega 5), linoleic acid (omega 6), palmitoleic acid (omega 7), oleic acid (omega 9), arachidonic acid, polyunsaturated fatty acids, pantothenic acid, and dicarboxylic acids: maleic acid, fumaric acid, succinic acid, and adipic acid;

(¶) The retinoids will include retinol (the form of vitamin A found in mammals), retinoic acid and retinoids generally (such as 9-cis-retinoic acid used in cancer therapy);

(¶) Alpha-Lipoic acid (thioctic acid; 1,2-dithiolane-3-pentanoic acid) will include dihydrolipoic acid and other derivatives, as well as cysteine, and methionine;

(¶) The coenzyme Q analogs will include ubiquinone and idebenone, as well as similar structures such as plastoquinone, ubiquinol, and trolox;

(¶) The vitamins will include A, A1-A3, C, D, D1-D7, E, G, H (biotin), I, K, M, Q, and U;

(¶) A variety of other substances are also included such as caffeic acid, coumaric acid, chlorogenic acid, vanillic acid, ferulic acid, and nicotinic acid; the carotenoids, flavonoids, resveratrol, epigallocatechin, and epigallocatechin-3-gallate; KAPA (7-keto-8-aminopelargonic acid), and DAPA (7,8-diaminopelargonic acid); and polyphenols, genistein, curcumin, and delphinidin.

V. Conjugated Complexes of an Antioxidant and a Carrier Molecule

Conjugates of the entire class of synthesized biochemical carrier molecules—i.e., the acyclic (alkyl) carnitinoid analog carriers, and/or the cycloalkyl carnitinoid analog carriers, and/or the glycocarnitinoid analog carriers—can be prepared by combining any one of the three types of carnitinoid analog carriers with an acid, its acid chloride (or a corresponding activated ester form) of the chosen antioxidant composition under standard reaction conditions.

The resulting conjugates—i.e., the coupled antioxidant-carnitinoid analog carrier complexes—are interchangeable surrogates of acyl CoA; and these purposefully prepared conjugated complexes comprising at least one antioxidant (and desirably as many as three antioxidants) covalently bonded and reversibly attached to a synthetic carrier molecule will localize to and pass through both the outer and the inner membranes of the mitochondria within a living cell.

It will be noted and appreciated also that a primary feature and major advantage of this covalent linkage and reversibly attached mode of antioxidant juncture to the carrier molecule is that the absolute stereochemistry of the beta or "β"-hydroxyl group (analogous to that of natural L-carnitine) is maintained in each of the synthetic carnitinoid analog carriers; and a person ordinarily skilled in the art of chemical synthesis can prepare coupled complexes of the chosen antioxidant composition and each type of carnitinoid analog carrier using conventionally known synthesis methods and reaction procedures [see for example: Piermatti et al, Synthesis and characterization of carnitine-nitro derivatives, *Bioorg Med Chem* 16:1444-1451, 2008; Jain et al, 3-Azido-3-deoxy-glycopyranoside derivatives as scaffolds for the synthesis of carbohydrate-based universal pharmacophore mapping libraries, *Bioorg Med Chem Lett* 13:2185-2189, 2003; Hutchison et al, Stereoselective synthesis of a conformationally defined cyclohexyl carnitine analogue that binds CPT-1 with high affinity, *Bioorg Med Chem* 7:1505-1511, 1999; Sofia et al, Carbohydrate-based small molecule scaffolds for the construction of universal pharmacophore mapping libraries, *J Org Chem* 63:2802-2803, 1998; Wang et al, Synthesis and characterization of long chain alkyl acyl carnitine esters. Potentially biodegradable cationic lipids for use in gene delivery, *J Med Chem* 41:2207-2215, 1998; Billhardt et al, Enzymatic methods for the preparation of acetyl-CoA and analogs, *Bioorg Chem* 17:1-12, 1989; Ogawa et al, Synthesis of hexa-N—O-acetyl-DL-hydroxyvalidamine, *Chem Lett* 1559-1562, 1980; and Baer H H, Cyclizations of dialdehydes with nitromethane. VIII. A spontaneous epimerization in aci-nitro glycosides and its significance in the preparation of derivatives of 3-amino-3-deoxy-D-mannose, -D-glucose, -D-talose and D-galactose, *J Am Chem Soc* 84:83-89, 1962].

Moreover, the synthetic carnitinoid analog carriers—after capturing and holding an antioxidant moiety via reaction with any available hydroxy group—will transverse the outer and inner mitochondrial membranes. These capabilities and physiological functions are based on empirical results obtained via specific assay determinations [see U.S. Pat. No. 6,280,981; Dykens et al, High-throughput assessment of mitochondrial membrane potential in situ using fluorescence resonance energy transfer, *Mitochondrion* 1:461-473, 2002; and Dykens J A & Will Y, The significance of mitochondrial toxicity testing in drug development, *Drug Discovery Today* 12:777-785, 2007].

These assays accurately and precisely assess the effects of test antioxidant compositions on the following criteria:

(i) Mitochondrial membrane potential ($\Delta\Psi_m$);

(ii) Collapse of $\Delta\Psi_m$ mediated by $Ca^{2+}$ overload (including mitochondrial permeability transition);

(iii) Activation of caspase-3 induced by apoptotic stimulation;

(iv) Glutamate-mediated excitotoxic death in primary rat neuronal cultures; and (v) Toxicity to SHSY-5Y neuroblastoma cells with and without exogenous oxidative stress.

The common denominator in these evaluation assays is the combination of oxidative stress and $Ca^{2+}$ dysregulation known to undermine mitochondrial integrity and yield necrosis and/or apoptosis. All these assays were performed in a blinded format; and, unless otherwise specified, were examined in SHSY-5Y neuroblastoma cells [as per Dykens et al, High-throughput assessment of mitochondrial membrane potential in situ using fluorescence resonance energy transfer, *Mitochondrion* 1:461-473, 2002]. The empirical data and results obtained via these assays are presented subsequently hereinafter.

Particular Reaction Schemes

Illustrative of the synthesis reactions which yield mitochondria-targeting, antioxidant/carnitinoid analog ester complexes are those given below.

For the acyclic (alkyl) carnitine analog carriers, the conjugated complex yielding reactions are governed by Reaction Schemes A1-A3 as stated below.

Reaction Scheme A1:

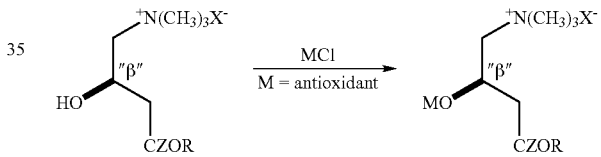

Reaction Scheme A2:

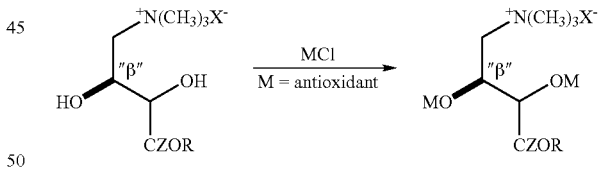

Reaction Scheme A3:

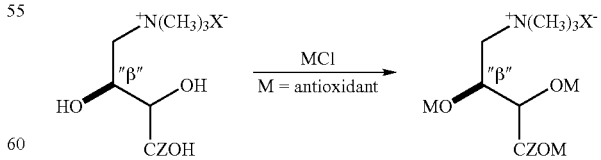

For the cycloalkyl analog carriers, the conjugated complex yielding reactions are exemplified and illustrated by the cyclohexyl-based analogs and Reaction Schemes B1-B5, as shown below.

Reaction Scheme B1:
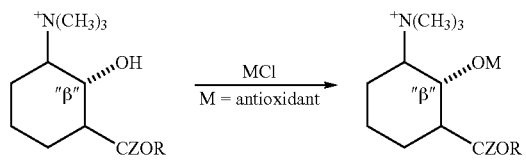
Reaction Scheme B2:
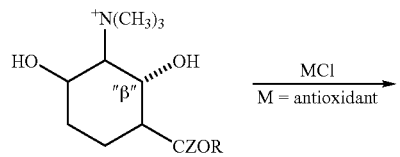
Reaction Scheme B3:
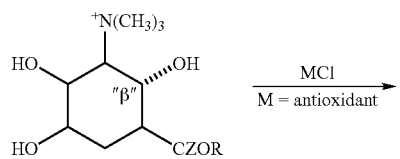
Reaction Scheme B4:
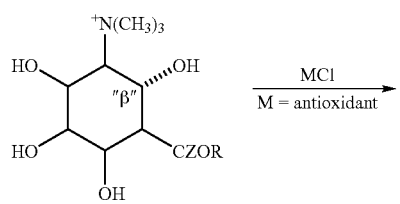
Reaction Scheme B5:
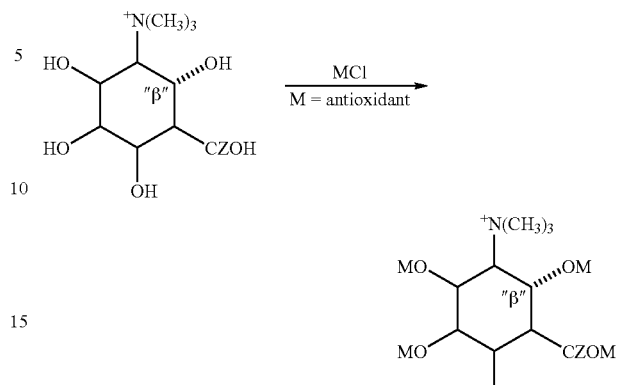
For the glycocarnitinoid carriers, the coupled complex yielding reactions are illustrated using the aldopyranose-sugar carnitine analog carriers and by Reaction Schemes C1(a)-C1(c), as given below.
Reaction Scheme C1(a):
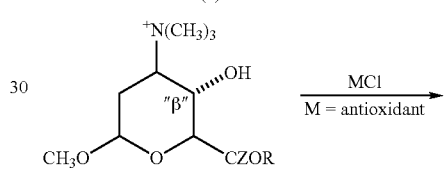
Reaction Scheme C1(b):
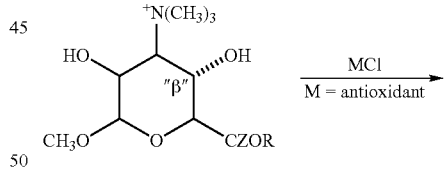
Reaction Scheme C1(c):
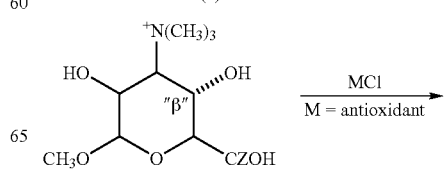

-continued

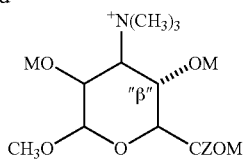

Figure 2:
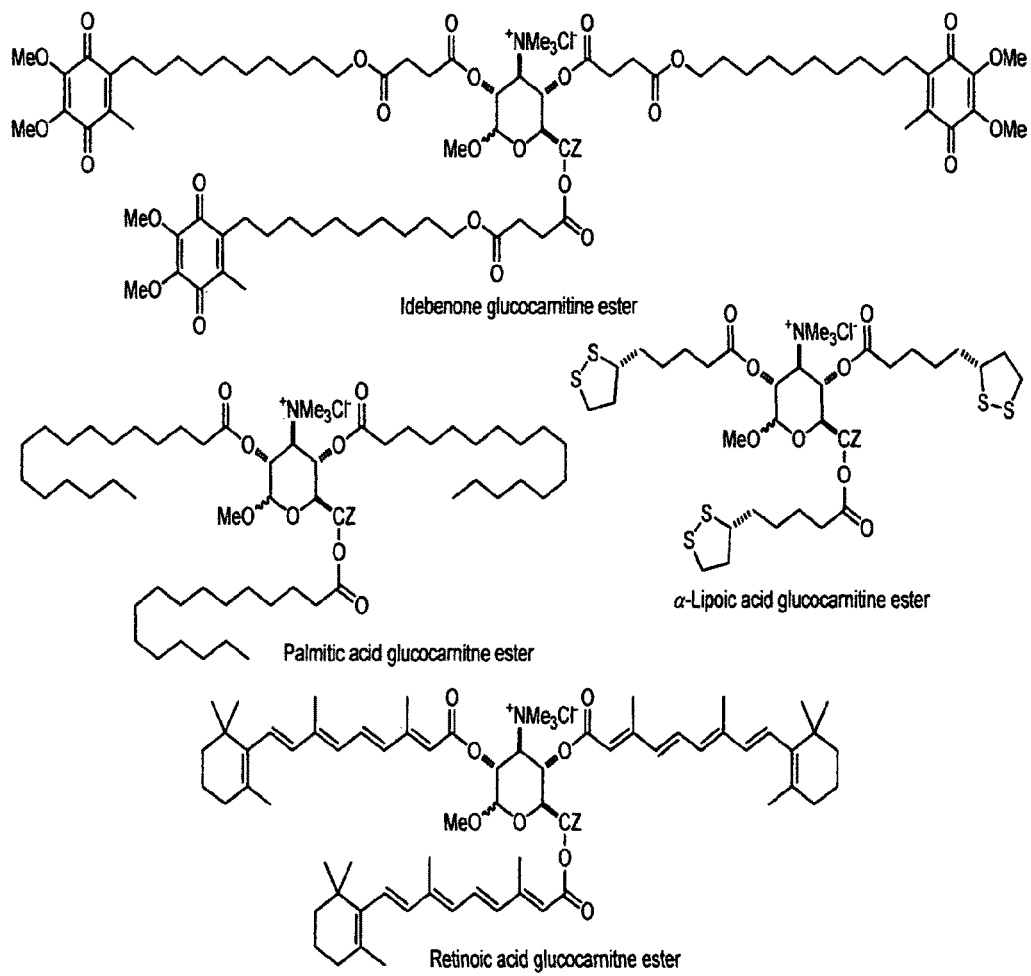
FIG. 2 illustrates the stereochemical structural formulas of four individual embodiments of the glucose-based carnitine analog carrier.

In addition, several other illustrative, but non-limiting examples of coupled antioxidant-carrier complexes prepared in accordance with Reaction Scheme C1(c) are shown by FIG. 2. It will be recognized that a major advantage of using such aldose-based analogs as the carrier molecule is that three (3) molecules of the chosen antioxidant become reversibly attached via covalent bond linkages (directly or through a linking molecule) to the carrier structure. Consequently, three molecules (rather than only one) of the chosen antioxidant will then become available as therapeutic medicaments within the mitochondria of the living cell.

VI. The Methodology of the Present Invention

In general, the present invention provides a broad methodology for prophylactically treating normal mitochondria, as well as for therapeutically treating impaired or damaged mitochondria, in a living cell under in-vitro, ex-vivo, and/or in-vivo conditions. While the methodology is intended primarily as a mode of therapeutic treatment for mitochondrial-associated diseases and disorders, these treatment procedures may also be employed as preventative and prophylactic measures in those life instances where no clinical diagnosis of a pathological state has yet been made—as for example, in slowing down manifestations and symptoms of degenerative aging, the pre-onset of Parkinson's disease, Alzheimer's disease, diabetes, and cancer.

Thus, the method for treating the mitochondria of a living cell will broadly comprise the following manipulative steps and human actions:
  obtaining a coupled antioxidant-carrier complex which is comprised of a carrier molecule which
    (i) is a biocompatible carnitinoid analog composition which does not exist in nature,
    (ii) has a carnitinoid analog structure comprising three to seven carbon atoms,
    (iii) presents and maintains the stereochemistry of at least one hydroxyl group similar to that of the beta-hydroxyl group in natural L-carnitine for on-demand reaction with and reversible attachment to a biologically active antioxidant,
    (iv) is a chiral and non-racemic synthetic composition,
    (v) includes a functional group presented either as a carboxylic acid; or as an ester, an alcohol, or an ether with an aliphatic moiety or an aromatic moiety or a combination of both, and
    (vi) optionally presents at least one other hydroxyl group available for on-demand reaction with and reversible attachment of another biologically active antioxidant;
  and an antioxidant which has reacted with and become reversibly attached to at least one available hydroxyl group to yield said coupled antioxidant-carrier complex;
  introducing said coupled antioxidant-carrier complex to a living cell;
  permitting said introduced coupled antioxidant-carrier complex to target and become localized within the mitochondria of the living cell; and
  allowing said localized coupled antioxidant-carrier complex to release the antioxidant within the mitochondria for reaction with such reactive oxygen species as may then be present.

A. Routes of Administration, Frequency of Administration, and Dosages

Accordingly, the coupled antioxidant-carrier complexes described above can be administered under in-vivo conditions in any appropriate formulation for oral, topical, subcutaneous, intradermal, intramuscular, intragastric, intravenous, iontophoresis, or parenteral administration to a living host subject. In addition, other modes of in-vivo administration, such as perfusion and lavage, may be advantageously employed as well.

These formulated preparations can be introduced by any means that brings access to normal or damaged cells within the tissues and organs in the host body. The preferred routing and mode of administration will typically be chosen by the clinician, physician or surgeon, or other medical professional to meet and accommodate the particular pathological affliction, the patient's current health and condition, and the overall prognosis for the disease or disorder in question.

The dosage to be administered and frequency of administration will, of course, vary and be dependent upon the age, health, and weight of the intended recipient; the kind of concurrent treatment, if any; the duration of treatment, and the degree of the therapeutic effect ultimately desired.

B. Pharmaceutical Formulations and Preparations

The question of suitable pharmaceutical formulations will be decided and vary with the chosen mode of in-vivo administration. For example, if the prepared in-advance coupled complexes are to be administered topically, they can be admixed in a concentration range in a pharmaceutically inert topical blending agent such as a gel, an ointment, a lotion, or a cream; and which may include such blending agents as water, glycerol, alcohol, propylene glycol, fatty alcohols, triglycerides, fatty acid esters, or mineral oils. Other topical blending agents are represented by liquid petrolatum, isopropyl palmitate and the like. In addition, minerals such as viscosity stabilizers and the like may be added if and when necessary.

In the alternative, if the prepared in-advance coupled complexes are to be given internally (i.e., parenterally), these substances will be prepared in sterile form; in multiple or single dose formats; and dispersed in a fluid carrier such as sterile physiological saline, or 5% dextrose solutions commonly used with injectables.

VII. The Treatment System of the Invention

The present invention also provides a general systematic approach for the treatment of mitochondrial-associated diseases and disorders. The pre-chosen antioxidants are delivered to and become localized within the mitochondria of a living cell; and after being localized in the interior of the mitochondria, can be used either prophylactically for prevention or therapeutically for ameliorating specific diseases and disorders. For example, the antioxidant may be used to protect the aerobic oxidations mechanism from radiation or from reactive oxygen species; or the antioxidant can be used therapeutically to target anticancer or pro-apoptotic derivatives.

Accordingly, the treatment system may be defined as follows.

A system for targeted delivery of an antioxidant to the mitochondria of a living cell comprising:
a coupled antioxidant-carrier complex comprised of
a carrier molecule for the reversible attachment and release of an antioxidant, and which
(i) is a biocompatible carnitinoid analog structure which does not exist in nature,
(ii) is comprised of three to seven carbon atoms,
(iii) presents and maintains the stereochemistry of at least one hydroxyl group similar to that of the beta-hydroxyl group in natural L-carnitine for on-demand reaction with and reversible attachment to a biologically active antioxidant,
(iv) is a chiral and non-racemic synthetic composition,
(v) includes a functional group presented either as a carboxylic acid; or as an ester, an alcohol, or an ether with an aliphatic moiety or an aromatic moiety or a combination of both, and
(vi) optionally presents at least one other hydroxyl group available for on-demand reaction with and reversible attachment to another biologically active antioxidant, and
an antioxidant which has reacted with and become reversibly attached to an available hydroxyl group of said carnitinoid analog composition to form a coupled carrier complex; and
means for introducing said coupled antioxidant-carrier complex to a living cell whereby said introduced coupled antioxidant-carrier complex targets and become localized within the mitochondria of the living cell, and whereby said antioxidant becomes released within the mitochondria for reaction with such reactive oxygen species as may then be present.

Treatable Diseases and Disorders

The Treatment Focus and Objective

The system of treatments provided by the present invention directly acts and operatively functions within a living cell to achieve two specific goals and purposes: (a) To mitigate and control the degree of injury and damage then presently existing within an impaired or damaged mitochondria—the therapeutic effect; and (b) to prevent such unimpaired and undamaged mitochondria as then are present within the cell from attack and injury in the future from reactive oxygen species.

It will be noted and appreciated, therefore, that the present invention does not and cannot act directly against the true causative agent or verified positive source that brings about a pathological medical condition or produces an injurious clinical effect. Instead, the focus and objective of the present invention are the active protection and/or remedial therapy of the metabolic oxidation systems within the mitochondria of the living cell then serving to produce energy (ATP); and, via the effective delivery and localization of pre-chosen antioxidants to the living cell in-situ, thereby to attack, to react with, and to neutralize effectively such reactive oxygen species as are then released as concomitant byproducts by the pathology of the true causative agent or verified positive source.

The Treatable Diseases and Disorders

The present invention can be effectively used to treat all mitochondrial-associated diseases and disorders generally. Merely illustrating the currently recognized range and variety of mitochondrial-associated diseases and disorders are the following: mitochondrial dementia, Parkinson's disease, Huntington's disease, Alzheimer's disease, amyotrophic lateral sclerosis, diabetes, steatohepatitis, retinopathies, ischemia-reperfusion injury, the effects of aging, the effects of radiation sickness, cardiomyopathies, and metabolic and neurodegenerative disorders.

The Treatable Neoplasms

In addition, defects in mitochondrial function are known to contribute to the development and progression of many kinds of cancers [Czarnecka et al, Cancer as a mitochondriopathy, *J Cancer Molecules* 3:71-79, 2007]. For this reason, many embodiments of the conjugated antioxidant-carrier complexes will utilize those antioxidant compositions which have been demonstrably shown to be active and functional as anti-tumor agents.

Merely exemplifying and representing the various kinds of antioxidant compositions able to serve as antitumor agents are:

(1) Antimetabolites including the folic acid analogs (such as Methotrexate), the pyrimidine analogs (such as Fluorouracil, Gemcitabine, or Cytarabine), and the purine analogs (such as Mercaptopurine or Thioguanine);

(2) Alkylating agents including the Nitrogen Mustard types, the Alkyl Sulfonate types, the Nitrosourea types, and the Triazene types;

(3) Natural Products including the Vinca Alkaloids, the Taxanes, the Epothilones, the Calicheamycins, the Macrolides, the Jasmonates, the Camptothecins, the Epipodophyllotoxins, certain Antibiotics, and specific Enzymes; and (4) A variety of miscellaneous agents such as platinum coordination complexes, substituted urea, methyl hydrazine derivatives, tyrosine kinase inhibitors, estrogens and antiestrogens, androgens and antiandrogens, progestins and antiprogestins, and adrenocortical suppressants.

Accordingly a meaningful range of neoplasms (tumors) can be treated. Among these are the malignant neoplasms known as: colorectal cancer, breast cancer, ovarian cancer, cervical cancer, hepatic cancer, leukemias, lymphomas, multiple myeloma, oesophageal cancer, pancreatic cancer, prostate cancer, testicular cancer, thyroid cancer, neuroblastoma, glioma, and bladder, head and neck, and lung cancers among others.

VIII. Advantages and Benefits Provided by the Invention

The subject matter as a whole comprising the present invention offers substantive advantages and provides long desired benefits to clinicians and medical practitioners, as well as to the intended living recipients. These include the following:

1. The chemical analogs and methodology of the present invention can be employed to advantage with any mitochondrial-associated disease and/or disorder. These mitochondrial-associated diseases and disorders not only include infectious diseases and organ disorders; but also encompass solid tumor cells and non-disseminating clinical cancers, among many others.

2. The present invention provides for a selective uptake by mitochondria within those cells, tissues and organs most affected by mitochondrial oxidative damage.

3. The present invention offers an effective blocking of oxidative damage within mitochondria, coupled with the ability either to recycle the active form of antioxidant within mitochondria or to allow the antioxidant to be removed by the dynamic waste elimination systems of the living subject.

4. The present invention allows a physician to prescribe an appropriate dosage and treatment regimen; and to introduce and deliver a clinically efficacious antioxidant composition at dosage concentrations well below that threshold amount or determined value which will cause toxicity or other harmful side effects in-vivo.

5. The present invention provides for long-term administration of one or more pre-chosen antioxidant compositions which preferably have a natural process of accumulation and removal in-vivo, thereby limiting its uptake and enabling the antioxidant concentration to enter into a steady-state distribution within the living host.

IX. Experiments and Empirical Data

To demonstrate the merits and value of the present invention, a series of planned experiments and empirical data are presented below. It will be expressly understood, however, that the experiments described and the results provided are merely the best evidence of the subject matter as a whole which is the invention; and that the empirical data, while limited in content, is only illustrative of the scope of the invention envisioned and claimed.

Experimental Series 1

Effects on Mitochondrial Membrane Potential ($\Delta\Psi_m$)

Assay Protocol

The mitochondrial membrane potential ($\Delta\Psi_m$) was recorded in intact and digitonin-permeabilized cells using a well documented assay [see U.S. Pat. No. 6,280,981]. This assay is based on fluorescence resonance energy transfer (FRET) between two dyes: a nonyl acridine orange (NAO; Molecular Probes Inc.), which stains cardiolipin, lipid found exclusively in the mitochondrial inner membrane; and tetramethylrhodamine (TMRE; Molecular Probes Inc.), a potentiometric dye taken up by mitochondria in accord with Nernstian dictates potential and concentration. The presence of TMRE quenches NAO emission in proportion to $\Delta\Psi_m$, whereas a loss of $\Delta\Psi_m$ with consequent efflux of TMRE dequenches NAO.

The high specificity of NAO staining; the selective monitoring of the fluorescence emitted by NAO, not TMRE; and the stringent requirement for co-localization of both dyes within the mitochondrion—all act in concert to allow the FRET assay to report $\Delta\Psi_m$, unconfounded by background signal arising from potentiometric dye responding to plasma membrane potential [see Dykens et al, High-throughput assessment of mitochondrial membrane potential in situ using fluorescence resonance energy transfer, *Mitochondrion* 1:461-473, 2002].

This FRET-based $\Delta\Psi_m$, assay is a sensitive and reliable in situ indicator of mitochondrial membrane potential and mitochondrial integrity. The method readily detects and distinguishes between agents that: collapse $\Delta\Psi_m$ (CCCP $EC_{50}$=2 µM); hyperpolarize $\Delta\Psi_m$ (oligomycin $EC_{50}$=26 nM); prevent $Ca^{2+}$ uptake via uniporter inhibition (ruthenium red $EC_{50}$=0.27 µM, RU-360 $EC_{50}$=12 nM); inhibit $Ca^{2+}$-mediated $\Delta\Psi_m$ loss (bongkrekate $EC_{50}$=77 nM); inhibit secondary permeability transition (cyclosporin A $EC_{50}$=0.31 µM); dissipate $\Delta\Psi_m$ under physiological circumstances (ADP $EC_{50}$=122 µM).

The Substances Undergoing Testing

The carnitinoid analog compounds undergoing test are those identified as Compounds 1-10 respectively, as shown by FIGS. 3 and 4.

Test Procedures

The individual compounds (Nos. 1-10) described within FIGS. 3 and 4 were examined for the above responses in two screens using intact SHSY-5Y neuroblastoma cells permeabilized with 0.01% digitonin according to the method of Dykens cited above.

Plasma membrane potential is no longer a confounding issue when cells are permeabilized, and the increased bioavailability at the mitochondrion maximizes likelihood of detecting efficacy. In this protocol, cells are permeabilized while in the plate reader, and $\Delta\Psi_m$ collapse is induced via direct addition of $Ca^{2+}$.

Test Screening

In the first test screening assay, compounds 1-10 were individually examined in intact SHSY-5Y neuroblastoma cells, @ 1 µM as singletons (N=5). In the second screening assay, compounds 1-10 were individually run in triplicate over a 6-log concentration range (N=2).

To illustrate, the response of each compound Nos. 1-10 respectively is compared to untreated cells on the same plate; and the data are expressed within Table E1 presented below as % $Ca^{2+}$ response. Those individual compounds that effectively repress maximal $Ca^{2+}$ uptake, or that moderate secondary permeability transition, have scores lower than the maximal $Ca^{2+}$ response. Ineffective compounds are indistinguishable from $Ca^{2+}$ exposed controls.

By way of comparison, ruthenium red, cyclosporin A, and bongkrekic acid have scores of 9%, 27%, and 44%, respectively. The B-C response indicates whether the compound alone dissipates or hyperpolarizes $\Delta\Psi_m$; typical values for protonophore uncouplers such as CCCP are ~−1800, and for adenine nucleotide transporter inhibitors such as bongkrekate are ~−600. Values within ±200 RFU of controls are indistinguishable from controls.

TABLE E1

| Response of Compounds @ 1 µM in FRET-Based $\Delta\Psi_m$ Assay | | |
|---|---|---|
| Compound (see FIG. 3-4) | % $Ca^{2+}$ Response (± SE, N = 5) | B-C Response (RFU) |
| 1 | 79.8 ± 15.2 | −219 |
| 2 | 101.3 ± 6.3 | −211 |
| 3 | 58.4 ± 17.2 | −74 |
| 4a | 125.8 ± 12.9 | −218 |
| 4b | 113.9 ± 17.9 | −128 |
| 7d | 98.6 ± 23.0 | −119 |
| 8a | 125.9 ± 21.9 | −187 |
| 9c | 113.0 ± 14.2 | −237 |
| 9d | 65.5 ± 17.4 | −154 |
| 10c | 69.4 ± 25.7 | −26 |
| 10d | 100.4 ± 19.2 | −152 |

Results

As may be seen and concluded from the data in Table E1, compounds 4a and 8a exacerbate $Ca^{2+}$-induced collapse of $\Delta\Psi_m$; whereas, at 1 µM concentration, compounds 3, 9d, and 10c weakly moderate it. At this 1 µM concentration, several of the compounds dissipated $\Delta\Psi_m$, but none of the tested compounds 1-10 appeared to hyperpolarize it.

Experimental Series 2

Dose Responses in FRET-Based $\Delta\Psi_m$ Assay

In this test series, compounds 1-10 were individually evaluated using the FRET-based $\Delta\Psi_m$ assay by employing a dose response format at 6 concentrations. The test concentrations started at 10 µM and then were decreased 5 logs to 0.1 nM, in accordance with the Dykens protocol cited above.

Each test concentration was run in triplicate for the compounds (Nos. 1-10); and each test series was identically repeated twice. The observed responses were expressed as % untreated controls, with the data being analyzed for nonlinear regression and plotted using Prism software as illustrated graphically by FIGS. 5, 6, and 7 respectively. As stated above, both the effects for each compound alone, as well as the potential effects on $Ca^{2+}$-mediated $\Delta\Psi_m$ collapse, were evaluated and empirically determined.

Results

At the 10 µM concentration, compound Nos. 1-4b, 8a, 10c and 10d substantially dissipated $\Delta\Psi_m$. This result occurred fairly consistently in the case of compound 4a, and was also quite consistent for compounds 10c and 10d. Note that the moderation of $\Delta\Psi_m$ collapse observed at the 1 µM concentration (see the data of Table E1 above) is likely a consequence of the dissipation reported here; and the magnitude of the $\Delta\Psi_m$ collapse is diminished to the extent that the compounds had already dissipated potential. Also, at the 10 µM concentration, compound Nos. 2, 3, 4a, 4b, 9c, 9d, 10c, and 10d were found to reduce the magnitude of acute $\Delta\Psi_m$ collapse by $Ca^{2+}$ overload.

Figures 5, 5A:
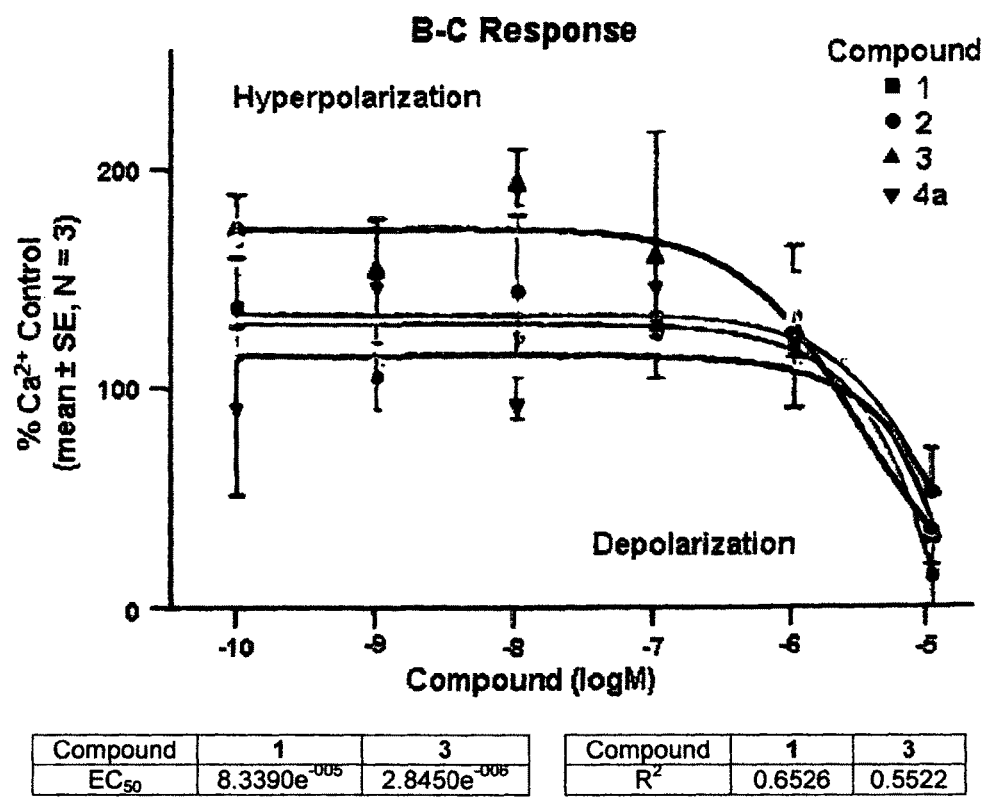
FIGS. 5A and 5B are graphs illustrating some specific capabilities and properties for synthesized compounds 1-4a respectively.
Figure 5B:
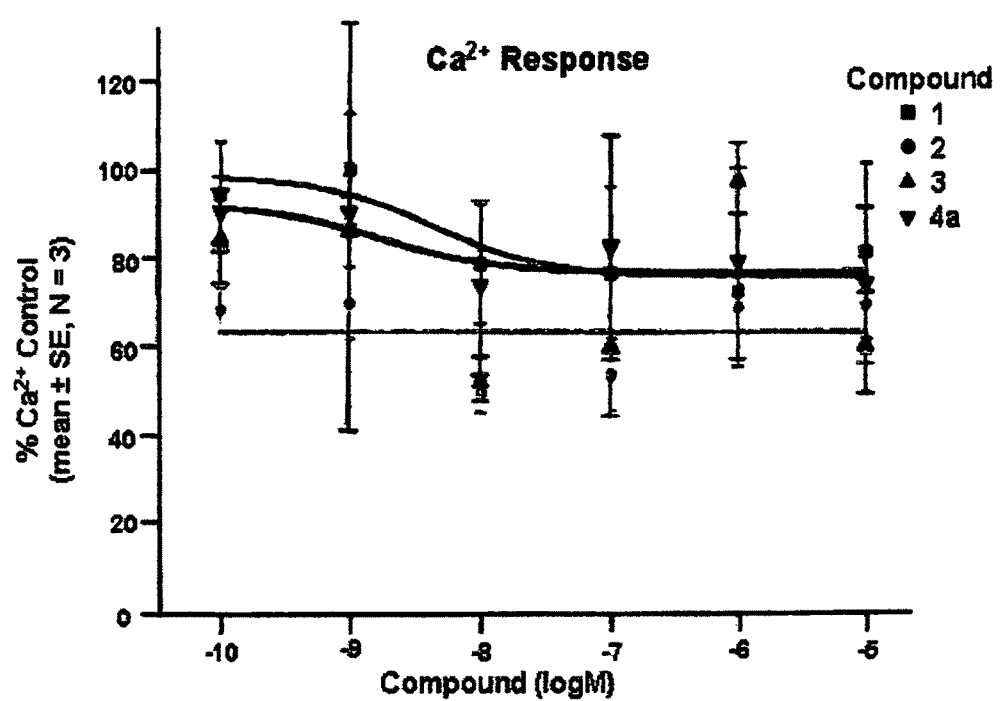
Figures 6, 6A:
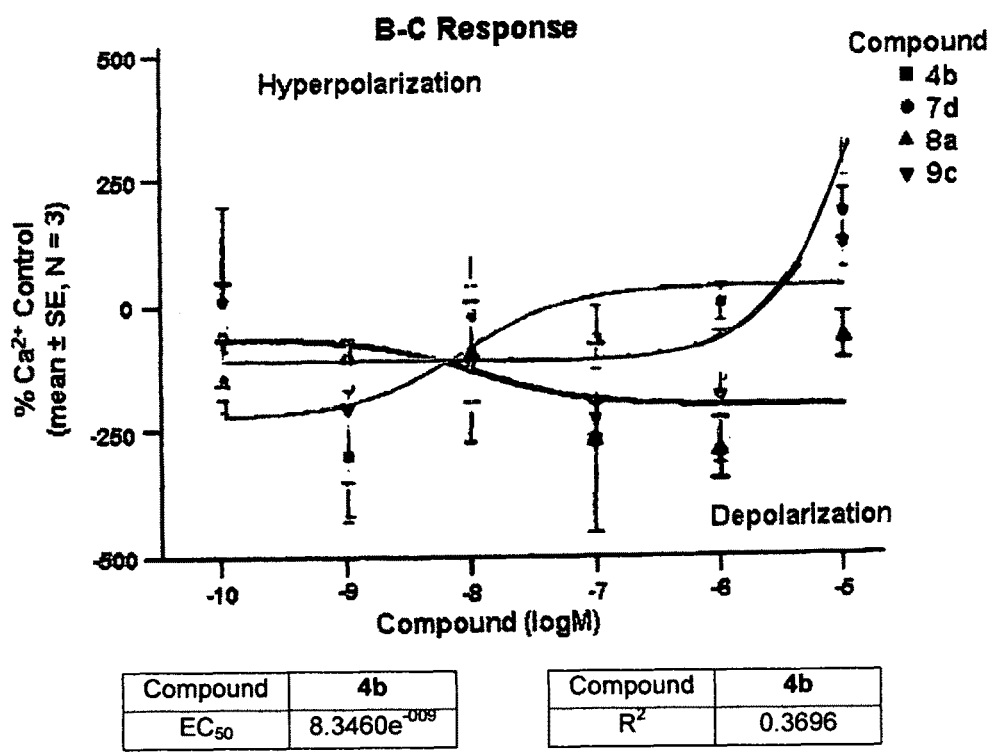
FIGS. 6A and 6B are graphs illustrating some specific capabilities and properties for synthesized compounds 4b, 7d, 8a, and 9c respectively.
Figure 6B:
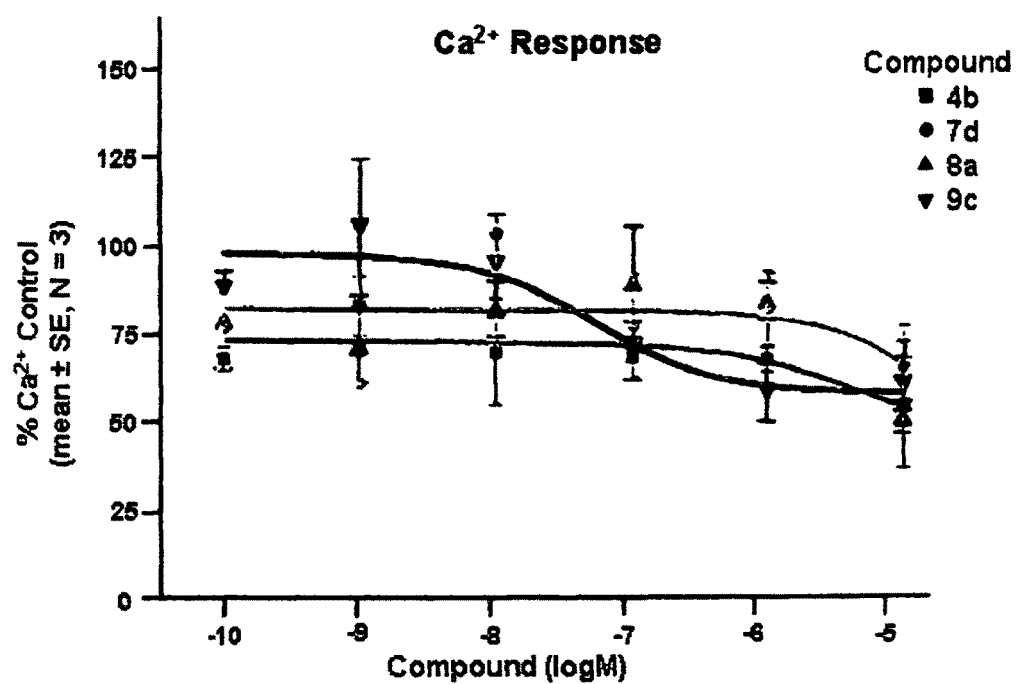
Figures 7, 7A:
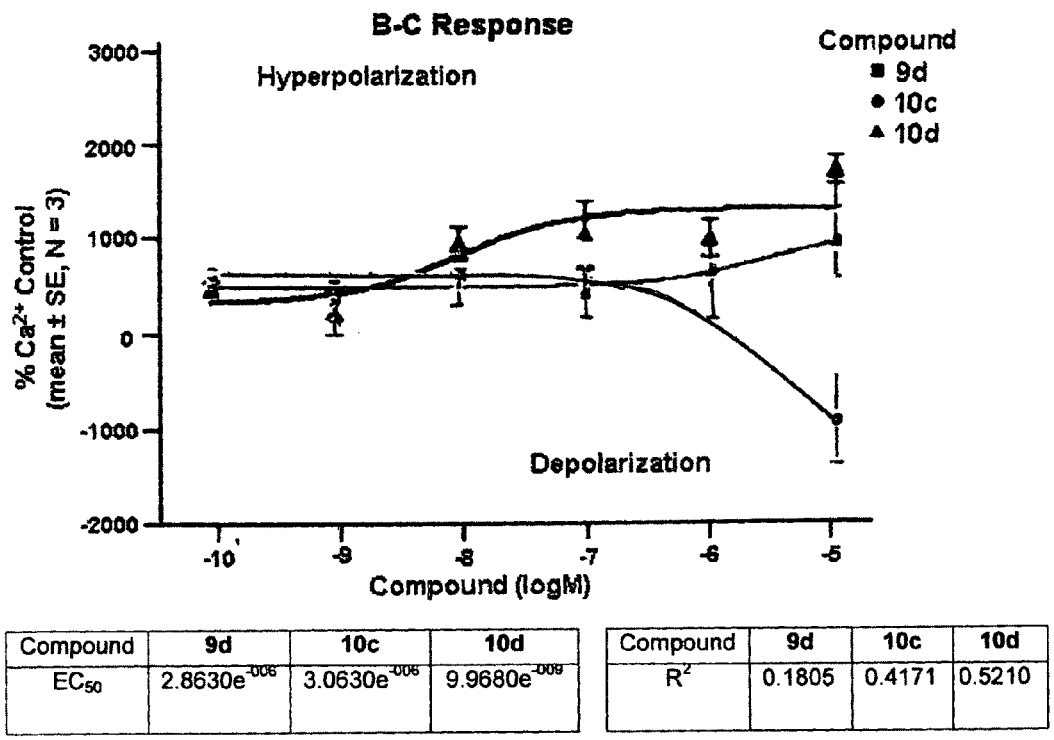
FIGS. 7A and 7B are graphs illustrating some specific capabilities and properties for synthesized compounds 9d, 10c and 10d respectively.
Figure 7B:
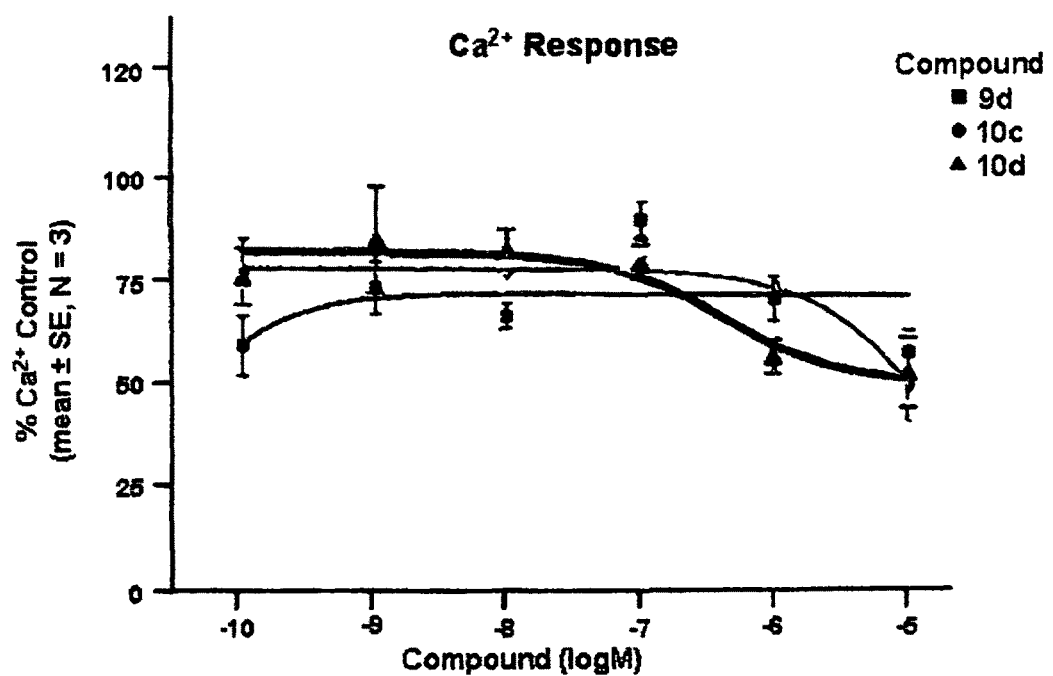

Empirical data for the compounds are graphically shown in FIGS. 5, 6 and 7 respectively. Please note that FIGS. 5A, 6A and 7A each graphically represents the effect of the indicated compound alone on $\Delta\Psi_m$, while FIGS. 5B, 6B and 7B respectively each graphically show the dose response to $Ca^{2+}$-induced $\Delta\Psi_m$ collapse.

Experimental Series 3

Caspase-3 Activation

It is expected that compounds that can moderate $Ca^{2+}$-mediated $\Delta\Psi_m$ collapse will also inhibit cytochrome c release, and thus correspondingly moderate the resulting activation of caspase-3. The potential ability of test compound Nos. 1-10 individually to moderate caspase activation was therefore examined using SHSY-5Y cells, in accordance with the Dykens assay.

In the Dykens assay method, caspase activation is induced by 24 hr exposure to a combined stress of ethacrynic acid (25 to derivatize glutathione and induce oxidative stress, and thapsigargin (1 µM), to induce a chronic increase in cytosolic $Ca^{2+}$. Caspase activity is determined using a fluorogenic substrate, with rates normalized to cell number; and is expressed as % response of controls on every plate exposed to ethacrynate and thapsigargen in the absence of compound. Compound Nos. 1-10 at 10 µM were separately introduced for reaction at the same time as the ethycrynic acid/thapsigargin addition, and were present throughout the 24 hr incubation period.

Results

At the 10 µM concentration, none of the 10 compounds tested significantly repressed caspase-3 activation. In comparison, the positive control (IGF-1) reduced activity by 64%.

Experimental Series 4

Cytotoxicity

The potential toxicity of test compound Nos. 1-10 was assessed in a 96-well format according to the Dykens assay method using uptake, de-esterification and retention of a cytosolic fluorescent dye as the live-dead criterion. The empirical data are normalized to untreated controls on the same plate.

Test Protocol

Procedurally, cells are exposed to the individual compound under test @ 3, 10, 30 and 100 µM concentrations for 24 hr, after which cell viability is measured. In addition, the potential of the test compounds to protect against chronic oxidative stress is determined by exposing cells for 24 hr to each individual test compound plus 5 µM ethacrynic acid, an agent that derivatizes cellular glutathione—thereby eliciting an oxidative load. Each test compound was individually tested in triplicate on two different days.

Results

None of the tested compounds (Nos. 1-10) was toxic alone. At the 10 µM concentration, compound 3 reduced cell death induced by ethacrynic acid by 23% and 35% in the two replicates; and compound 10d reduced death by 25% and 40%, respectively.

Experimental Series 5

Glutamate Toxicity

Excessive stimulation of glutamate receptors is among the most pathologically relevant models of neuronal cell death associated with mitochondrial failure and/or dysfunction. Accordingly, the 10 test compounds were individually evaluated in a glutamate toxicity assay.

Test Protocol

In these experiments, neurons are exposed to glutamate plus glycine (at 100 µM and 10 µM concentrations) for 10 minutes; and neuron cell viability is assessed at 24 hours time post-glutamate exposure by measuring the LDH activity in the culture media.

In this viability assay, the neuron cells are pretreated with compound [@ 0.3, 1, 3, 10, or 30 µM concentrations] for 10 minutes prior to glutamate stimulation. In addition, the test compound is present during the glutamate stimulation as well as during the 24 hr post-stimulation interval. These conditions facilitate both the detection of compounds that are toxic to neurons by themselves, as well as those that might be protective at any step in the cell death pathway. Neuron cells treated with glutamate plus compound were then compared to those neurons treated with glutamate alone.

Results

At the 30 µM concentration, compound Nos. 7d and 8a increased glutamate toxicity on all 4 days of testing. A significant effect was not observed at the lower concentrations.

The present invention is not to be limited in scope nor restricted in form except by the claims appended hereto:

What I claim is:

1. A preformed coupled antioxidant-carrier complex for in-situ reaction with such reactive oxygen species as may then be present within the interior of mitochondria in a living cell, said coupled antioxidant-carrier complex being an interchangeable surrogate of acyl CoA thioesters and consisting essentially of:

an acyclic (alkyl) carnitinoid analog carrier molecule having the stereo-chemical structure of

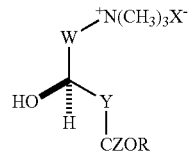

wherein W and Y are each independently comprised of one to three carbon atoms and selected from the group consisting of $C(Z_1Z_2)$, $C(Z_1Z_2)C(Z_3Z_4)$, and $C(Z_1Z_2)C(Z_3Z_4)C(Z_5Z_6)$ where $Z_1$, $Z_2$, $Z_3$, $Z_4$, $Z_5$, and $Z_6$ each are independently a carbonyl oxygen atom, or a null atom which satisfies carbon valency, or a hydrogen atom, or a hydroxyl group, where Z is a carbonyl oxygen atom, or two hydrogen atoms, where R is a lone-pair of electrons (zwitterion), or a hydrogen atom, or is an aliphatic moiety, or an aromatic moiety, or a combination of both aliphatic and aromatic moieties, and where X is a negatively charged ion, and wherein said acyclic (alkyl) carnitinoid analog carrier molecule (i) presents at least one discrete hydroxyl group in a stereochemical position analogous to the beta-hydroxyl group in naturally occurring carnitine for chemical reaction, said stereochemically positioned hydroxyl group being in direct reversible attachment to and detachment from a pre-chosen biologically active non-metal antioxidant, (ii) optionally presents at least a second discrete hydroxyl group available for on-demand reaction with and reversible attachment to a second biologically active non-metal antioxidant, (iii) is capable of entering into a living cell in-situ and passing into the interior of mitochondria then present within that living cell, (iv) demonstrably allows for the subsequent release of a reversibly bound biologically active non-metal antioxidant in-situ within the interior of mitochondria then present in that living cell; and at least one pre-chosen, biocompatible and biologically active non-metal antioxidant which (α) has covalently bonded with and become reversibly attached to at least one hydroxyl group of said acyclic (alkyl) carnitinoid analog carrier molecule to form a coupled antioxidant-carrier complex (β) is chemically devoid of metal constituents, (γ) can be transported into the interior of mitochondria in a living cell by said acyclic (alkyl) carnitinoid analog carrier molecule as a coupled antioxidant-carrier complex, (δ) will be released as a discrete entity from said acyclic (alkyl) carnitinoid analog carrier molecule into the interior of mitochondria in a living cell, (ε) is biologically active after release from a coupled antioxidant-carrier complex for in-situ reaction, and (ζ) will react after release from a coupled antioxidant-carrier complex with such reactive oxygen species as may then be present within the interior of mitochondria in a living cell.

2. A preformed coupled antioxidant-carrier complex for in-situ reaction with such reactive oxygen species as may then be present within the interior of mitochondria in a living cell, said coupled antioxidant-carrier complex being an interchangeable surrogate of acyl CoA thioesters and consisting essentially of:

A cycloalkyl carnitinoid analog carrier molecule having the stereo-chemical structure of

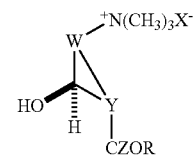

wherein W and Y are each independently comprised of one to three carbon atoms and selected from the group consisting of $C(Z_1Z_2)$, $C(Z_1Z_2)C(Z_3Z_4)$, and $C(Z_1Z_2)C(Z_3Z_4)C(Z_5Z_6)$ where $Z_1$, $Z_2$, $Z_3$, $Z_4$, $Z_5$, and $Z_6$ each are a null atom which satisfies carbon valency, or a hydrogen atom, or a hydroxyl group, where Z is a carbonyl oxygen atom, or two hydrogen atoms, where R is a lone-pair of electrons (zwitterion), or a hydrogen atom, or is an aliphatic moiety, or an aromatic moiety, or a combination of both aliphatic and aromatic moieties, and where X is a negatively charged ion, and wherein said cycloalkyl carnitinoid analog carrier molecule (i) presents at least one discrete hydroxyl group in a stereochemical position analogous to the beta-hydroxyl group in naturally occurring carnitine for chemical reaction, said stereochemically positioned hydroxyl group being in direct reversible attachment to and detachment from a pre-chosen biologically active non-metal antioxidant, (ii) optionally presents at least a second discrete hydroxyl group available for on-demand reaction with and reversible attachment to a second biologically active non-metal antioxidant, (iii) is capable of entering into a living cell in-situ and passing into the interior of mitochondria then present within that living cell, (iv) demonstrably allows for the subsequent release of a reversibly bound biologically active non-metal antioxidant in-situ within the interior of mitochondria then present in that living cell; and at least one pre-chosen, biocompatible and biologically active non-metal antioxidant which (α) has covalently bonded with and become reversibly attached to at least one hydroxyl group of said cycloalkyl carnitinoid analog carrier molecule to form a coupled antioxidant-carrier complex (β) is chemically devoid of metal constituents, (γ) can be transported into the interior of mitochondria in a living cell by said cycloalkyl carnitinoid analog carrier molecule as a coupled antioxidant-carrier complex, (δ) will be released as a discrete entity from said cycloalkyl carnitinoid analog carrier molecule into the interior of mitochondria in a living cell, (ε) is biologically active after release from a coupled antioxidant-carrier complex for in-situ reaction, and (ζ) will react after release from a coupled antioxidant-carrier complex with such reactive oxygen species as may then be present within the interior of mitochondria in a living cell.

3. A preformed coupled antioxidant-carrier complex for in-situ reaction with such reactive oxygen species as may then be present within the interior of mitochondria in a living cell, said coupled antioxidant-carrier complex being an interchangeable surrogate of acyl CoA thioesters and consisting essentially of:

A five or six carbon monosaccharide glycocarnitinoid analog carrier molecule having the stereo-chemical structure of

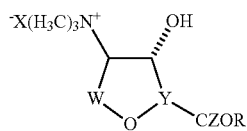

wherein W and Y are each independently comprised of one to two carbon atoms and selected from the group consisting of $C(Z_1Z_2)$ and $C(Z_1Z_2)C(Z_3Z_4)$ where $Z_1$, $Z_2$, $Z_3$, $Z_4$ each are independently a carbonyl oxygen atom, or a null atom which satisfies carbon valency, or a hydrogen atom, or a hydroxyl group, where Z is a carbonyl oxygen atom, or two hydrogen atoms, where R is a lone-pair of electrons (zwitterion), or a hydrogen atom, or is an aliphatic moiety, or an aromatic moiety, or a combination of both aliphatic and aromatic moieties, and where X is a negatively charged ion, and wherein said glycocarnitinoid analog carrier molecule (i) presents at least one discrete hydroxyl group in a stereochemical position analogous to the beta-hydroxyl group in naturally occurring carnitine for chemical reaction, said stereochemically positioned hydroxyl group being in direct reversible attachment to and detachment from a pre-chosen biologically active non-metal antioxidant, (ii) optionally presents at least a second discrete hydroxyl group available for on-demand reaction with and reversible attachment to a second biologically active non-metal antioxidant, (iii) is capable of entering into a living cell in-situ and passing into the interior of mitochondria then present within that living cell, (iv) demonstrably allows for the subsequent release of a reversibly bound biologically active non-metal antioxidant in-situ within the interior of mitochondria then present in that living cell; and at least one pre-chosen, biocompatible and biologically active non-metal antioxidant which (α) has covalently bonded with and become reversibly attached to at least one hydroxyl group of said glycocarnitinoid analog carrier molecule to form a coupled antioxidant-carrier complex (β) is chemically devoid of metal constituents, (γ) can be transported into the interior of mitochondria in a living cell by said glycocarnitinoid analog carrier molecule as a coupled antioxidant-carrier complex, (δ) will be released as a discrete entity from said glycocarnitinoid analog carrier molecule into the interior of mitochondria in a living cell, (ε) is biologically active after release from a coupled antioxidant-carrier complex for in-situ reaction, and (ζ) will react after release from a coupled antioxidant-carrier complex with such reactive oxygen species as may then be present within the interior of mitochondria in a living cell.

4. A system for targeted delivery of an antioxidant into the mitochondria of a living cell comprising:

a preformed coupled antioxidant-carrier complex for in-situ reaction with such reactive oxygen species as may then be present within the interior of mitochondria in a living cell, said coupled antioxidant-carrier complex being an interchangeable surrogate of acyl CoA thioesters and consisting essentially of:

an acyclic (alkyl) carnitinoid analog carrier molecule having the stereo-chemical structure of

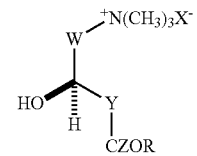

wherein W and Y are each independently comprised of one to three carbon atoms and selected from the group consisting of $C(Z_1Z_2)$, $C(Z_1Z_2)C(Z_3Z_4)$, and $C(Z_1Z_2)C(Z_3Z_4)C(Z_5Z_6)$ where $Z_1$, $Z_2$, $Z_3$, $Z_4$, $Z_5$, and $Z_6$ each are independently a carbonyl oxygen atom, or a null atom which satisfies carbon valency, or a hydrogen atom, or a hydroxyl group, where Z is a carbonyl oxygen atom, or two hydrogen atoms, where R is a lone-pair of electrons (zwitterion), or a hydrogen atom, or is an aliphatic moiety, or an aromatic moiety, or a combination of both aliphatic and aromatic moieties, and where X is a negatively charged ion, and wherein said acyclic (alkyl) carnitinoid analog carrier molecule (i) presents at least one discrete hydroxyl group in a stereochemical position analogous to the beta-hydroxyl group in naturally occurring carnitine for chemical reaction, said stereochemically positioned hydroxyl group being in direct reversible attachment to and detachment from a pre-chosen biologically active non-metal antioxidant, (ii) optionally presents at least a second discrete hydroxyl group available for on-demand reaction with and reversible attachment to a second biologically active non-metal antioxidant, (iii) is capable of entering into a living cell in-situ and passing into the interior of mitochondria then present within that living cell, (iv) demonstrably allows for the subsequent release of a reversibly bound biologically active non-metal antioxidant in-situ within the interior of mitochondria then present in that living cell, and at least one pre-chosen, biocompatible and biologically active non-metal antioxidant which (α) has covalently bonded with and become reversibly attached to at least one hydroxyl group of said acyclic (alkyl) carnitinoid analog carrier molecule to form a coupled antioxidant-carrier complex (β) is chemically devoid of metal constituents, (γ) can be transported into the interior of mitochondria in a living cell by said acyclic (alkyl) carnitinoid analog carrier molecule as a coupled antioxidant-carrier complex, (δ) will be released as a discrete entity from said acyclic (alkyl) carnitinoid analog carrier molecule into the interior of mitochondria in a living cell, (ε) is biologically active after release from a coupled antioxidant-carrier complex for in-situ reaction, and (ζ) will react after release from a coupled antioxidant-carrier complex with such reactive oxygen species as may then be present within the interior of mitochondria in a living cell;

and a biocompatible preparation for introducing said coupled antioxidant-carrier complex to a living cell, whereby said introduced coupled antioxidant-carrier complex targets and become localized within the interior of the mitochondria of the living cell, and whereby said coupled antioxidant becomes released within the mitochondria and is biologically active after release within the interior of the mitochondria for in-situ reaction with such reactive oxygen species as may then be present.

5. A system for targeted delivery of an antioxidant into the mitochondria of a living cell comprising:

a preformed coupled antioxidant-carrier complex for in-situ reaction with such reactive oxygen species as may then be present within the interior of mitochondria in a living cell, said coupled antioxidant-carrier complex being an interchangeable surrogate of acyl CoA thioesters and consisting essentially of:

A cycloalkyl carnitinoid analog carrier molecule having the stereo-chemical structure of

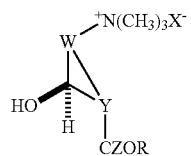

wherein W and Y are each independently comprised of one to three carbon atoms and selected from the group consisting of $C(Z_1Z_2)$, $C(Z_1Z_2)C(Z_3Z_4)$, and $C(Z_1Z_2)C(Z_3Z_4)C(Z_5Z_6)$ where $Z_1$, $Z_2$, $Z_3$, $Z_4$, $Z_5$, and $Z_6$ each are a null atom which satisfies carbon valency, or a hydrogen atom, or a hydroxyl group, where Z is a carbonyl oxygen atom, or two hydrogen atoms, where R is a lone-pair of electrons (zwitterion), or a hydrogen atom, or is an aliphatic moiety, or an aromatic moiety, or a combination of both aliphatic and aromatic moieties, and where X is a negatively charged ion, and wherein said cycloalkyl carnitinoid analog carrier molecule (i) presents at least one discrete hydroxyl group in a stereochemical position analogous to the beta-hydroxyl group in naturally occurring carnitine for chemical reaction, said stereochemically positioned hydroxyl group being in direct reversible attachment to and detachment from a pre-chosen biologically active non-metal antioxidant, (ii) optionally presents at least a second discrete hydroxyl group available for on-demand reaction with and reversible attachment to a second biologically active non-metal antioxidant, (iii) is capable of entering into a living cell in-situ and passing into the interior of mitochondria then present within that living cell, (iv) demonstrably allows for the subsequent release of a reversibly bound biologically active non-metal antioxidant in-situ within the interior of mitochondria then present in that living cell, and at least one pre-chosen, biocompatible and biologically active non-metal antioxidant which (α) has covalently bonded with and become reversibly attached to at least one hydroxyl group of said cycloalkyl carnitinoid analog carrier molecule to form a coupled antioxidant-carrier complex (β) is chemically devoid of metal constituents, (γ) can be transported into the interior of mitochondria in a living cell by said cycloalkyl carnitinoid analog carrier molecule as a coupled antioxidant-carrier complex, (δ) will be released as a discrete entity from said cycloalkyl carnitinoid analog carrier molecule into the interior of mitochondria in a living cell, (ε) is biologically active after release from a coupled antioxidant-carrier complex for in-situ reaction, and (ζ) will react after release from a coupled antioxidant-carrier complex with such reactive oxygen species as may then be present within the interior of mitochondria in a living cell;

and a biocompatible preparation for introducing said coupled antioxidant-carrier complex to a living cell, whereby said introduced coupled antioxidant-carrier complex targets and become localized within the interior of the mitochondria of the living cell, and whereby said coupled antioxidant becomes released within the mitochondria and is biologically active after release within the interior of the mitochondria for in-situ reaction with such reactive oxygen species as may then be present.

6. A system for targeted delivery of an antioxidant into the mitochondria of a living cell comprising:

a preformed coupled antioxidant-carrier complex for in-situ reaction with such reactive oxygen species as may then be present within the interior of mitochondria in a living cell, said coupled antioxidant-carrier complex being an interchangeable surrogate of acyl CoA thioesters and consisting essentially of:

A five or six carbon monosaccharide glycocarnitinoid analog carrier molecule having the stereo-chemical structure of

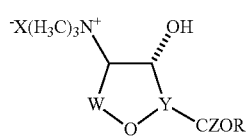

wherein W and Y are each independently comprised of one to two carbon atoms and selected from the group consisting of $C(Z_1Z_2)$ and $C(Z_1Z_2)C(Z_3Z_4)$ where $Z_1$, $Z_2$, $Z_3$, and $Z_4$ each are independently a carbonyl oxygen atom, or a null atom which satisfies carbon valency, or a hydrogen atom, or a hydroxyl group, where Z is a carbonyl oxygen atom, or two hydrogen atoms, where R is a lone-pair of electrons (zwitterion), or a hydrogen atom, or is an aliphatic moiety, or an aromatic moiety, or a combination of both aliphatic and aromatic moieties, and where X is a negatively charged ion, and wherein said glycocarnitinoid analog carrier molecule (i) presents at least one discrete hydroxyl group in a stereochemical position analogous to the beta-hydroxyl group in naturally occurring carnitine for chemical reaction, said stereochemically positioned hydroxyl group being in direct reversible attachment to and detachment from a pre-chosen biologically active non-metal antioxidant, (ii) optionally presents at least a second discrete hydroxyl group available for on-demand reaction with and reversible attachment to a second biologically active non-metal antioxidant, (iii) is capable of entering into a living cell in-situ and passing into the interior of mitochondria then present within that living cell, (iv) demonstrably allows for the subsequent release of a reversibly bound biologically active non-metal antioxidant in-situ within the interior of mitochondria then present in that living cell, and at least one pre-chosen, biocompatible and biologically active non-metal antioxidant which (α) has covalently bonded with and become reversibly attached to at least one hydroxyl group of said glycocarnitinoid analog carrier molecule to form a coupled antioxidant-carrier complex (β) is chemically devoid of metal constituents, (γ) can be transported into the interior of mitochondria in a living cell by said glycocarnitinoid analog carrier molecule as a coupled antioxidant-carrier complex, (δ) will be released as a discrete entity from said glycocarnitinoid analog carrier molecule into the interior of mitochondria in a living cell, (ε) is biologically active after release from a coupled antioxidant-carrier complex for in-situ reaction, and (ζ) will react after release from a coupled antioxidant-carrier complex with such reactive oxygen species as may then be present within the interior of mitochondria in a living cell;

and a biocompatible preparation for introducing said coupled antioxidant-carrier complex to a living cell, whereby said introduced coupled antioxidant-carrier complex targets and become localized within the interior of the mitochondria of the living cell, and whereby said coupled antioxidant becomes released within the mitochondria and is biologically active after release within the interior of the mitochondria for in-situ reaction with such reactive oxygen species as may then be present.

7. The coupled antioxidant-carrier complex as recited in claim 1, 2, or 3 wherein said carnitinoid analog composition presents at least two hydroxyl groups for on-demand reaction with and juncture of a biologically active antioxidant.

8. The coupled antioxidant-carrier complex as recited in claim 1, 2, or 3 wherein said carnitinoid analog composition presents at least three hydroxyl groups for on-demand reaction with and juncture of a biologically active antioxidant.

9. The coupled antioxidant-carrier complex as recited in claim 1, 2, or 3 wherein said antioxidant is an organic fatty acid or an unsaturated or polyunsaturated fatty acid or a dicarboxylic acid.

10. The coupled antioxidant-carrier complex as recited in claim 1, 2, or 3 wherein said antioxidant is selected from the group consisting of retinol, retinoic acid and retinoids.

11. The coupled antioxidant-carrier complex as recited in claim 1, 2, or 3 wherein said antioxidant is selected from the group consisting of cysteine, methionine, alpha-lipoic acid, dihydrolipoic acid, ubiquinone and its analogs, idebenone, plastoquinone, and trolox.

12. The coupled antioxidant-carrier complex as recited in claim 1, 2, or 3 wherein said antioxidant is selected from the group consisting of vitamins A, A1-A3, C, D, D1-D7, E, G, H (biotin), I, K, M, Q, and U; caffeic acid, coumaric acid, chlorogenic acid, vanillic acid, ferulic acid, oleic acid, nicotinic acid, carotenoids, flavonoids, resveratrol, epigallocatechin, epigallocatechin-3-gallate, polyphenols, genistein, curcumin, delphinidin, KAPA (7-keto-8-aminopelargonic acid), and DAPA (7,8-diaminopelargonic acid).

13. The coupled antioxidant-carrier complex as recited in claim 1, 2, or 3 which has been prepared as a pharmaceutical formulation.

14. The coupled antioxidant-carrier complex as recited in claim 1, 2, or 3 wherein said antioxidant has demonstrable antitumor properties.

15. The system as recited in claim 4, 5, or 6 wherein said biocompatible preparation for introducing said coupled antioxidant-carrier complex to a living cell is performed under ex-vivo, in-vitro, or in-vivo circumstances.

16. The system as recited in claim 4, 5, or 6 wherein said biocompatible preparation for introducing said coupled antioxidant-carrier complex are selected from the group consisting of oral, topical, subcutaneous, intradermal, intramuscular, intragastric, intravenous, iontophoresis, or parenteral administration.

* * * * *